United States Patent [19]

Thomas et al.

[11] Patent Number: 5,409,897
[45] Date of Patent: Apr. 25, 1995

[54] CYSTEINE-MODIFIED ACIDIC FIBROBLAST GROWTH FACTOR AND METHODS OF USE

[75] Inventors: Kenneth A. Thomas, Chatham Burough; David L. Linemeyer, Westfield, both of N.J.

[73] Assignee: Merck & Co., Inc., Rahway, N.J.

[21] Appl. No.: 189,230

[22] Filed: Jan. 31, 1994

Related U.S. Application Data

[60] Division of Ser. No. 30,510, Mar. 12, 1993, Pat. No. 5,312,911, which is a division of Ser. No. 938,310, Aug. 28, 1992, Pat. No. 5,223,483, which is a continuation of Ser. No. 759,128, Sep. 10, 1991, abandoned, which is a continuation of Ser. No. 244,431, Sep. 16, 1988, abandoned, which is a continuation-in-part of Ser. No. 112,600, Oct. 22, 1987, abandoned.

[51] Int. Cl.$^6$ .............................................. A61K 37/36
[52] U.S. Cl. .......................................... 514/12; 514/2; 514/8; 530/399
[58] Field of Search ................... 514/2, 8, 12; 530/399

[56] References Cited

U.S. PATENT DOCUMENTS

| | | | |
|---|---|---|---|
| 4,444,760 | 4/1984 | Thomas, Jr. et al. | 514/21 |
| 4,518,584 | 5/1985 | Mark et al. | 424/85.2 |
| 4,677,064 | 6/1987 | Mark et al. | 435/69.1 |
| 4,752,585 | 6/1988 | Koths et al. | 435/252.33 |
| 4,835,260 | 5/1989 | Shoemaker et al. | 531/347 |

FOREIGN PATENT DOCUMENTS

| | | |
|---|---|---|
| 131150 | 1/1985 | European Pat. Off. |
| 142344 | 5/1985 | European Pat. Off. |
| 225701 | 1/1987 | European Pat. Off. |
| 267795 | 11/1987 | European Pat. Off. |
| 298723 | 7/1988 | European Pat. Off. |
| 87/01728 | 3/1987 | WIPO |
| 87/05332 | 9/1987 | WIPO |

OTHER PUBLICATIONS

Ortega et eal. (1991) J. Biol. Chem. 266, 5842–5846.
Linemeyer et al. (1991) Growth Factors 3, 287.
Abraham et al., J. Cell Biochem. Supp. vol. 0. No. 11, Part A p. 50 (1987).
Anderson and Kingston, Proc. Natl. Acad. Sci. USA 80, pp. 6838–6842 (1983).
Armelin, Proc. Natl. Acad. Sci. USA 70, pp. 2702–2706 (1973).
Aviv and Leder, Proc. Natl. Acad. Sci USA 69, pp. 1408–1412 (1972).
Barritault et al., J. Neurosci. Res. 8, pp. 477–490 (1982).
Beaucage and Caruthers, Tetrahedron Letters 22, pp. 1859–1862 (1981).
Brosius, Gene 27, pp. 161–172 (1984).
DeBoer et al., Proc. Natl. Acad. Sci. USA 80, pp. 21–25 (1983).
Esch et al., Proc. Natl. Acad. Sci. USA 82, pp. 6507–6511 (1985).
Fiddes et al., J. Cell Biochem. vol. 32, Suppl. 10C, L146, p. 149 (1986).
Fourtanier et al., J. Invest. Dermatal. 87, pp. 76–80 (1986).
Gautschi–Sova et al., Biochem. Biophys. Res. Comm. 140, pp. 874–880 (1986).
Gentz et al., Proc. Natl. Acad. Sci. USA 78, pp.4936–4940 (1981).
Gimenez–Gallego et al., Science 230, pp. 1385–1388 (1985).
Gimenez–Gallego et al., Biochem. Biophys. Res. Commun. 138, pp. 611–617 (1986).
ospodarowicz et al., J. Cell Biol. 97, pp. 1677–1685 (1983).

(List continued on next page.)

*Primary Examiner*—Keith Baker
*Attorney, Agent, or Firm*—John W. Wallen, III; Jack L. Tribble; Jospeh F. DiPrima

[57] ABSTRACT

Mutant human acidic fibroblast growth factor proteins are recombinantly produced having replaced cysteine residues with amino acids incapable of disulfide bond formation. The recombinantly produced mutant human acidic fibroblast growth factor proteins have improved biological activity in the absence of heparin when compared to wild-type recombinant human acidic fibroblast growth factor.

18 Claims, 2 Drawing Sheets

OTHER PUBLICATIONS

Greisler et al., Tras. Am. Soc. Artif. Intern. Organs, vol. XXXII, 346–349 (1986).
Harper et al., Biochem. 25, pp. 4097–4103 (1986).
Hoffman, Growth 4, pp. 361–376 (1940).
Itakura et al., Sci. 198, pp. 1056–1063 (1977).
Jay et al., Science 23, pp. 541–545.
Kuo et al., Fed. Proc. 44, p. 695 (1985).
Linemeyer et al., Bio. Tech. 5, pp. 960–965 (1987).
Maniatis et al., Cell 15, pp. 687–701.
Matteucci and Caruthers, J. Am. Chem. Soc. 103, pp. 3185–3191 (1981).
Maxam and Gilbert, Proc. Natl. Acad. Sci., USA 74, pp. 560–564 (1977).
Maxam and Gilbert, Methods In Enzymology 65, pp. 499–560 (1980).
Norris et al., Nucleic Acids Res. 11, pp. 5103–5112 (1983).
O'Farrell, J. Biol. Chem. 250, pp. 4007–4021 (1975).
Sanger et al., Proc. Natl. Acad. Sci. USA 74, pp. 5463–5467 (1977).
Smithies et al., Science 202, pp. 1284–1289 (1987).
Suggs et al., Proc. Natl. Acad. Sci. USA 78, pp. 6613–6617 (1981).
Thomas et al., Proc. Natl. Acad. Sci. USA 81, pp. 357–361 (1984).
Thomas et al., Proc. Natl. Acad. Sci. USA 82, pp. 6409–6413 (1985).
Thomas and Gimenez-Gallego, TIBS 11, pp. 81–84 (1986).
Thomas et al., J. Biol. Chem. 255, pp. 5517–5520 (1980).
Trowell et al., J. Exp. Biol. 16, pp. 60–70 (1939).
Tseng et al., Eur. J. Biochem. 122, pp. 355–360 (1982).
Wensink et al., Cell 3, pp. 315–325 (1974).
Vlodavsky et al., J. Cell Biol. 83, pp. 468–486 (1979).
Zoller and Smith, Methods in Enzymology 100, pp. 468–500 (1983).
Zoller and Smith, DNA 3, pp. 479–488 (1984).
Bohlen et al., Proc. Natl. Acad. Sci. USA 81, pp. 5364–5368 (1984).
Burgess et al., Proc. Natl. Acad. Sci. USA 83, pp. 7216–7220 (1986).
Canalis et al., J. Clin. Invest. 79, pp. 52–58 (1987).
Crabb et al., Biochem., 25, pp. 4988–4993 (1986).
Esch et al., Biochem. Biophys. Res. Comm. 133, pp. 554–562 (1985).
Gimenez-Gallego et al., Biochem. Biophys. Res. Comm. 135, pp. 541–548 (1986).
Gospodarowicz et al., Proc. Natl. Acad. Sci. USA 73, pp. 4120–4124 (1976).
Gospodarowicz et al., Natl. Cancer Inst. Monog. 48, pp. 109–130 (1978).
Lemmon and Bradshaw, J. Cell. Biochem. 21, pp. 195–208 (1983).
Lobb and Fett, Biochem. 23, pp. 6296–6299 (1984).
Maciag et al., Science 225, pp. 932–935 (1984).
Maniatis et al., Molecular Cloning, A Lab., Cold Spring Harbor, N.Y. pp. 217–246, 270–294, 353–361 (1982).
Schoner et al., Proc. Natl. Acad. Sci. USA 83, pp. 8506–8510 (1986).
Schreiber et al., J. Cell Biol. 101, pp. 1623–1626 (1985).
Thomas et al., J. Prot. Chem. 6, pp. 163–171 (1987).
Seno, et al., Biochem. Biophys. Res. Comm. 151, pp. 701–708 (1988).

CYSTEINE-MODIFIED ACIDIC FIBROBLAST GROWTH FACTOR AND METHODS OF USE

RELATED U.S. APPLICATION DATA

This is a division of application Ser. No. 08/030,510, filed Mar. 12, 1993, now U.S. Pat. No. 5,312,911, which is a division of application 07/938,310, filed Aug. 28, 1992, U.S. Pat. No. 5,223,483, which is a continuation of application Ser. No. 07/759,128, filed Sep. 10, 1991, now abandoned, which is a continuation of application Ser. No. 07/244,431, filed Sep. 16, 1988, now abandoned, which is a continuation-in-part application of application Ser. No. 07/112,600, filed Oct. 22, 1987, now abandoned.

BACKGROUND OF THE INVENTION

Figure 1:
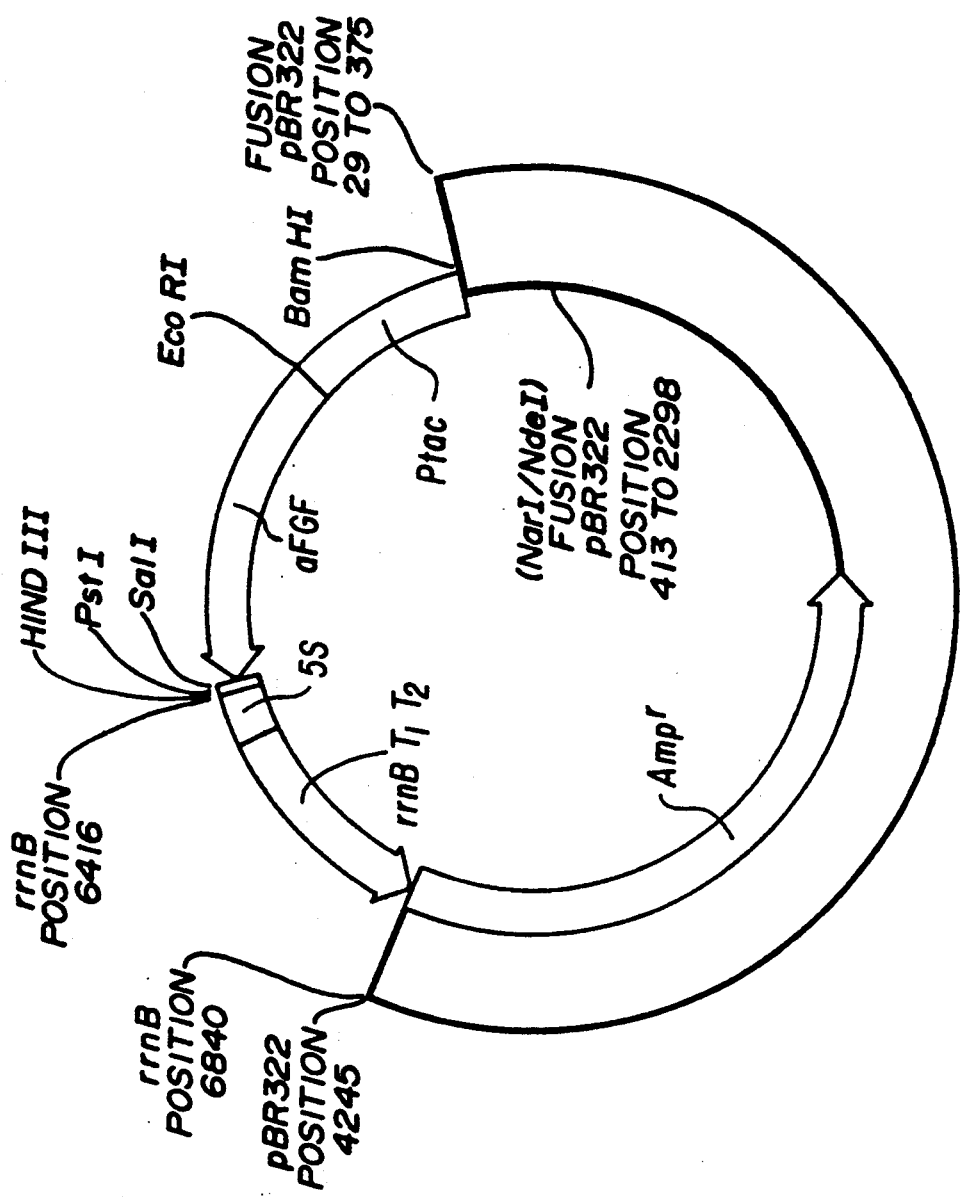
FIG. 1 is a diagram of the pKK223-3 plasmid containing a gene for mutant r-aFGF.

The discovery of substances that control the growth of animal cells, especially human cells, and the mechanism by which they work is currently one of the major focuses of biomedical research concerned with tissue repair and wound healing. Fibroblast growth factors (FGFs), mitogens for various cell types including many cells of mesodermal origin, have been identified and it has been suggested that they may induce mitosis which will result in tissue repair. Fibroblast mitogenic activity was first observed with extracts of tissue from the central nevous system. Brain-derived fibroblast mitogens were first described by Trowell et al., J. Exp. Biol. 16: 60–70 (1939) and Hoffman, Growth 4: 361–376 (1940). It was subsequently shown that pituitary extracts also had potent mitogenic activity for fibroblastoid cells, Amelin, Proc. Natl. Acad. Sci. USA 70: 2702–2706 (1973). Partial purification of both brain and pituitary fibroblast growth factor revealed mitogenic activity for a variety of cell types of differentiated cells including vascular endothelial cells, Gospodarowicz et al., Natl. Cancer Inst. Monogr. 48: 109–130 (1978). Fibroblast growth factor was originally thought to be a single peptide derived from the limited proteolysis of myelin basic protein. It has recently been shown that FGF exists in two forms, acidic FGF (aFGF) and basic FGF (bFGF), and both forms can be isolated and purified from mammalian brain, Thomas and Gimenez-Gallego, TIBS 11: 81–84 (1986). Numerous cell types respond to stimulation with either purified aFGF or bFGF to synthesize DNA and divide, including primary fibroblasts, vascular and corneal endothelial cells, chondrocytes, osteoblasts, myoblasts, smooth muscle, glial cells and neuroblasts, Esch et al., Proc. Natl. Acad. Sci. USA 82: 6507–6511 (1985); Kuo et al., Fed. Proc. 44: 695 (1985); Gensburger et al., C.R. Acad. Sc. Paris 303: 465–468 (1986). Pure bovine brain-derived aFGF not only acts as a potent mitogen for vascular endothelial cells in culture but also induces blood vessel growth in vivo, Thomas, et al. Proc. Natl. Acad. Sci. USA 82: 6409–6413 (1985). The mitogenic activity of purified aFGF can also be used to promote wound healing, Thomas, U.S. Pat. No. 4,444,760.

Acidic fibroblast growth factor was originally purified to homogeneity from bovine brain based on its mitogenic activity for BALB/c 3T3 fibroblasts, Thomas et al., Proc. Natl. Acad. Sci. USA 81: 357–361 (1984). This brain-derived growth factor has been repurified and renamed in multiple laboratories based both on its: mitogenic activity for vascular endothelial and astroglial cells (endothelial cell growth factor and astroglial growth factor 1), source (retinal-derived growth factor, eye-derived growth factor II, and perhaps brain-derived growth factor), and binding to heparin-Sepharose (class 1 heparin-binding growth factor or heparin-binding growth factor alpha), Thomas and Gimenez-Gallego TIBS 11: 81–84 (1986). The amino acid sequence of bovine aFGF has been determined, recognized to be highly homologous to basic FGF and related to the fibroblast mitogens interleukin 1-alpha and 1-beta, Gimenez-Gallego et al., Science 230: 1385–1388 (1985). The complete amino acid sequence of human aFGF has been determined from the purified protein, Gimenez-Gallego et al., Biochem. Biophy. Res. Comm. 138: 611–617 (1986), and from the gene, Jaye et al., Science 233: 541–545 (1986).

Native aFGF purified from brain or recombinant-derived aFGF (r-aFGF) requires the co-administration of heparin to optimally stimulate Balb/c 3T3 fibroblasts and vascular endothelial cells in culture. Human brain-derived and recombinant aFGF are only about 1% to 5% as active on these cells in culture in the absence of heparin compared to optimal activity in the presence of heparin. While the doses required for maximal aFGF activity are relatively low, it might be desirable to administer aFGF with no heparin since heparin could conceivably elicit detrimental side effects. Pure human aFGF, in addition to the standard conditions that destroy the activity of most proteins, extremes of heat, pH and the presence of proteases, is also labile to lyophilization and oxidation. The pure aFGF becomes cross-linked through intrachain or interchain disulfide bonds by oxidation and can be recovered in active form by disulfide reduction with 20 mM dithiothreitol. Heparin can inhibit intermolecular disulfide bond mediated aggregation of aFGF. This heterogeneous glycosaminoglycan has also been noted to stabilize aFGF from heat denaturation and proteolytic degradation by trypsin. Consequently, either exogenous or endogenous heparin is required for the in vivo activity associated with tissue repair. The present invention provides unique mutated forms of recombinant-derived aFGF which have an increased biological activity in the absence of heparin compared to native aFGF.

OBJECT OF THE INVENTION

It is, accordingly, an object of the present invention to convert by mutation recombinant bovine and human aFGF genes to genes capable of encoding proteins which are more active in the absence of heparin than the native or recombinant protein. Another object is to incorporate the specific genes into appropriate cloning vectors. A further object is to transform an appropriate host with each of the recombinant vectors and to induce expression of the specific mutated aFGF genes. Another object is to isolate and purify biologically active bovine and human mutated aFGF. These and other objects of the present invention will be apparent from the following description.

SUMMARY OF THE INVENTION

Novel genes coding for mutated bovine and human aFGF are constructed. The unique genes are derived from genes encoding recombinant native bovine and human aFGF by specific point mutation. Each gene construct is inserted into an expression vector which is used to transform an appropriate host. The transformed host cells produce unique mutated recombinant aFGF, human or bovine, which is purified and has enhanced or improved biological activity in the absence of heparin compared to the unmutated forms.

DETAILED DESCRIPTION

Acidic fibroblast growth factor exists in various microheterogeneous forms which are isolated from the various tissue sources and cell types known to contain aFGF. Microheterogeneous forms as used herein refer to a single gene product, that is a protein produced from a single gene unit of DNA, which is structurally modified following translation. These structural modifications, however, do not result in any significant alterations of biological activity of the peptide. Biological activity and biologically active are used interchangably and are herein defined as the ability of native, recombinant or mutant recombinant aFGF to stimulate DNA synthesis in quiescent Balb/c 3T3 fibroblasts as described in Example 7, to stimulate any of the cell types described above or to carry out any of the functions described in the art. The modifications may take place either in vivo or during the isolation and purification process. In vivo modification results in, but is not limited to, acetylation at the N-terminus, proteolysis, glycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in the production of microheterogeneous forms. The most common modification occuring during purification is proteolysis which is generally held to a minimum by the use of protease inhibitors. Under most conditions a mixture of microheterogeneous forms are present following purification of native aFGF. Native aFGF refers to aFGF isolated and purified from tissues or cells that contain aFGF.

The invention is contemplated to include all animal microheterogeneous forms of acidic fibroblast growth factor. The preferred embodiments include bovine and human microheterogeneous forms of aFGF. The most preferred microheterogeneous forms of bovine aFGF include a 154 amino acid form, a 140 amino acid form and a 134 amino acid form. The 140 amino acid form is shown in Table I, Gimenez-Gallego et al., Science 230: 1385-1388 (1985), and is the most preferred of the bovine species.

TABLE I

Amino Acid Sequence of Bovine aFGF

| 1 | 10 | 20 |
|---|---|---|
| PheAsnLeuProLeuGlyAsnTyrLysLysProLysLeuLeuTyrCysSerAsnGlyGlyTyrPheLeuArgIleLeu | | |

| 30 | 40 | 50 |
|---|---|---|
| ProAspGlyThrValAspGlyThrLysAspArgSerAspGlnHisIleGlnLeuGlnLeuCysAlaGluSerIleGlyGlu | | |

| 60 | 70 | 80 |
|---|---|---|
| ValTyrIleLysSerThrGluThrGlyGlnPheLeuAlaMetAspThrAspGlyLeuLeuTyrGlySerGlnThrProAsn | | |

| 90 | 100 | |
|---|---|---|
| GluGluCysLeuPheLeuGluArgLeuGluGluAsnHisTyrAsnThrTyrIleSerLysLysHisAlaGluLysHisTrp | | |

| 110 | 120 | 130 |
|---|---|---|
| PheValGlyLeuLysLysAsnGlyArgSerLysLeuGlyProArgThrHisPheGlyGlnLysAlaIleLeuPheLeuPro | | |

| 140 |
|---|
| LeuProValSerSerAsp |

The nucleotide sequence of the 140 amino acid form, recombinant, of bovine aFGF is shown in Table II.

TABLE II

Nucleotide Sequence of Bovine aFGF

| 1 | 20 | 40 |
|---|---|---|
| AATTCATGTTCAATCTGCCACTGGGTAATTACAAAAAGCCAAAGCTTCTTTACTGCTC | | |
| GTACAAGTTAGACGGTGACCCATTAATGTTTTTCGGTTTCGAAGAAATGACGAG | | |

| 60 | 80 | 100 |
|---|---|---|
| TAACGGTGGTTACTTTCTCCGCATCCTGCCAGATGGTACCGTGGACGGCACCAAAGATC | | |
| ATTGCCACCAATGAAAGAGGCGTAGGACGGTCTACCATGGCACCTGCCGTGGTTTCTAG | | |

| 120 | 140 | 160 |
|---|---|---|
| GTTCTGATCAACATATTCAACTGCAGCTGTGCGCCGAATCTATCGGTGAAGTTTACATCA | | |
| CAAGACTAGTTGTATAAGTTGACGTCGACACGCGGCTTAGATAGCCACTTCAAATGTAGT | | |

| 180 | 200 | 220 |
|---|---|---|
| AATCTACCGAAACTGGTCAATTCCTTGCCATGGACACTGATGGCCTGCTGTACGGATCCC | | |
| TTAGATGGCTTTGACCAGTTAAGGAACGGTACCTGTGACTACCGGACGACATGCCTAGGG | | |

TABLE II-continued

Nucleotide Sequence of Bovine aFGF

```
240                         260                         280
AGACCCCAAACGAGGAGTGCCTTTTCCTGGAGCGCCTGGAGGAAAACCATTACAACACCT
TCTGGGGTTTGCTCCTCACGGAAAAGGACCTCGCGGACCTCCTTTTGGTAATGTTGTGGA 300                         320                         340
ACATCTCTAAAAAGCATGCTGAGAAACATTGGTTCGTAGGCCTTAAGAAAAATGGCCGCT
TGTAGAGATTTTTCGTACGACTCTTTGTAACCAAGCATCCGGAATTCTTTTTACCGGCGA 360                         380                         400
CTAAACTGGGCCCTCGTACTCACTTTGGTCAAAAAGCTATCCTGTTCCTGCCACTGCCAG
GATTTGACCCGGGAGCATGAGTGAAACCAGTTTTTCGATAGGACAAGGACGGTGACGGTC 420                         440
TGAGCTCTGACTAATAGATATCG
ACTCGAGACTGATTATCTATAGCAGCT
```

The 154 amino acid form includes the following additional amino acids; Ala-Glu-Gly-Glu-Thr-Thr-Thr-Phe-Thr-Ala-Leu-Thr-Glu-Lys, with the carboxyl terminus Lys attached to the amino terminus Phe at the first position of the 140 amino acid form. The amino terminal alanine residue of the 154 amino acid form of the bovine aFGF may be acetylated. The 134 amino acid form is identical to the 140 amino acid form except that the first 6 amino acids of the amino terminus have been removed. When native aFGF is isolated the relative amounts of these microheterogeneous forms vary depending on the process used but generally contain at least two of these forms.

Human aFGF exhibits a similar microheterogeneity to that of bovine aFGF. The most preferred microheterogeneous forms of human aFGF include a 154 amino acid form, a 140 amino acid form and a 139 amino acid form. The human 140 amino acid form differs from the bovine form by eleven amino acids, as shown in TABLE VIII. The 154 amino acid form contains the exact sequence of the human 140 amino acid form plus the 14 additional amino acids associated with the bovine 154 amino acid form, with one exception. The amino acid at the fifth position of the N-terminus or at the −10 position as determined from the 140 amino acid Phe N-terminus in the human form is isoleucine and is substituted for the threonine in the bovine form. The additional 14 amino acid human N-terminal sequence is; Ala-Glu-Gly-Glu-Ile-Thr-Thr-Phe-Thr-Ala-Leu-Thr-Glu-Lys. The additional amino acids of the 154 amino acid form are numbered from the N-terminal Ala, −14, to the carboxyl terminal Lys, −1. The amino terminal alanine resiude at the −14 position may be acetylated. A third form of human aFGF contains 139 amino acids and is equivalent to the human 140 amino acid form with the amino terminal phenylalanine residue removed. The amino terminal asparagine residue may be deamidated to aspartic acid in the 139 amino acid form of human aFGF. The 140 and 139 amino acid forms are the most preferred forms of the human microheterogeneous forms. The 140 amino acid form is shown in Table III, Gimenez-Gallego et al., Biochem. Biophys. Res. Comm. 138: 611-617 (1986).

TABLE III

Amino Acid Sequence of Human aFGF

```
1                          10                          20
PheAsnLeuProProGlyAsnTyrLysLysProLysLeuLeuTyrCysSerAsnGlyGlyHisPheLeuArgIleLeu 30                         40                         50
ProAspGlyThrValAspGlyThrArgAspArgSerAspGlnHisIleGlnLeuGlnLeuSerAlaGluSerValGlyGlu 60                         70                         80
ValTyrIleLysSerThrGluThrGlyGlnTyrLeuAlaMetAspThrAspGlyLeuLeuTyrGlySerGlnThrProAsn 90                        100
GluGluCysLeuPheLeuGluArgLeuGluGluAsnHisTyrAsnThrTyrIleSerLysLysHisAlaGluLysAsnTrp 110                        120                        130
PheValGlyLeuLysLysAsnGlySerCysLysArgGlyProArgThrHisTyrGlyGlnLysAlaIleLeuPheLeuPro

140
LeuProValSerSerAsp
```

The nucleotide sequence of the 140 amino acid form, recombinant, of human aFGF is shown in Table IV.

TABLE IV

Nucleotide Sequence of Human aFGF

```
1                          20                         40                         60
AATTCATGTTCAATCTGCCACCGGGTAATTACAAAAAGCCAAAGCTTCTTTACTGCTCTA
              GTACAAGTTAGACGGTGGCCCATTAATGTTTTTCGGTTTCGAAGAAATGACGAGAT 80                        100                        120
ACGGTGGTCACTTTCTCCGCATCCTGCCAGATGGTACCGTGGACGGCACCAGAGATCGTT
TGCCACCAGTGAAAGAGGCGTAGGACGGTCTACCATGGCACCTGCCGTGGTCTCTAGCAA
```

TABLE IV-continued
Nucleotide Sequence of Human aFGF

```
                    140                          160                         180
CT GAT CAA CAT ATT CAA CTG CAG CTG TCC GCC GAA TCT GTC GGT GAA GTT TAC ATC AAA T
GA CTA GTT GTA TAA GTT GAC GTC GAC AGG CGG CTT AGA CAG CCA CTT CAA ATG TAG TTT A 200                          220                         240
CT ACC GAA ACT GGT CAA TAC CTT GCC ATG GAC ACT GAT GGC CTG CTG TAC GGA TCC AGA
GA TGG CTT TGA CCA GTT ATG GAA CGG TAC CTG TGA CTA CCG GAC GAC ATG CCT AGG GTC T 260                          280                         300
CCC CAA ACG AGG AGT GCC TTT TCC TGG AGC GCC TGG AGG AAA ACC ATT ACA ACA CCT ACA
GGG GTT TGC TCC TCA CGG AAA AGG ACC TCG CGG ACC TCC TTT TGG TAA TGT TGT GGA TGT 320                          340                         360
TCT CTA AAA AGC ATG CTG AGA AAA ATT GGT TCG TAG GCC TTA AGA AAA ATG GCA GCT GTA
AGA GAT TTT TCG TAC GAC TCT TTT TAA CCA AGC ATC CGG AAT TCT TTT TAC CGT CGA CAT 380                          400                         420
AAC GCG GCC CTC GTA CTC ACT ATG GCC AAA AAG CTA TCC TGT TCC TGC CAC TGC CAG TGA
TT GCG CCG GGA GCA TGA GTG ATA CCG GTT TTT CGA TAG GAC AAG GAC GGT GAC GGT CAC T

440
GCT CTG ACT AAT AGA TAT CG
CGA GAC TGA TTA TCT ATA GCA GCT
```

The preferred procedure for obtaining a gene for mammalian aFGF is to synthesize the gene because this allows optimization of translated protein and ease of mutagenesis. The gene may be synthesized based on the amino acid sequence of a microheterogeneous form of aFGF obtained from any animal including man. The preferred method is to use the bovine amino acid sequence for aFGF and chemically point mutate the base sequence, to produce the genes for other species, Linemeyer et al. Biotechnol. 5: 960–965 (1987).

The synthetic genes are based on the determined bovine amino acid sequence described by Gimenez-Gallego et al., Science 230: 1385–1388 (1985) and the human amino acid sequence as described by Gimenez-Gallego et al. Biochem. Biophys. Res. Comm., 138: 611–617 (1986) and shown in Tables I and III. The unique nucleotide sequence of the 140 amino acid form of bovine aFGF is derived from reverse translation of the amino acid sequence by a technique similar to that of Itakura et al., Science 198: 1056–1063 (1977). The various novel nucleotide sequences corresponding to the native amino acid sequence of bovine aFGF are shown in the following table:

TABLE V

```
        5                              10                          15                         20
Phe Asn Leu Pro Leu Gly Asn Tyr Lys Lys Pro Lys Leu Leu Tyr Cys Ser Asn Gly Gly
TTQ AAQ CTN CCN CTN GGN AAQ TAQ AAP AAP CCN AAP CTN CTN TAQ TGQ TCN AAQ GGN GGN
        TTP     TTP                             TTP TTP     AGQ 25                              30                          35                            40
Tyr Phe Leu Arg Ile Leu Pro Asp Gly Thr Val Asp Gly Thr Lys Asp Arg Ser Asp Gln
TAQ TTQ CTN CGN ATQ CTN CCN GAQ GGN ACN GTN GAQ GGN ACN AAP GAQ CGN TCN GAQ CAP
        TTP AGP ATA TTP                                             AGP AGQ 45                              50                          55                          60
His Ile Gln Leu Gln Leu Cys Ala Glu Ser Ile Gly Glu Val Tyr Ile Lys Ser Thr Glu
CAQ ATQ CAP CTN CAP CTN TGQ GCN GAP TCN ATQ GGN GAP GTN TAQ ATQ AAP TCN ACN GAP
        ATA     TTP     TTP             AGQ ATA                 ATA     AGQ 65                              70                          75                          80
Thr Gly Gln Phe Leu Ala Met Asp Thr Asp Gly Leu Leu Tyr Gly Ser Gln Thr Pro Asn
ACN GGN CAP TTQ CTN GCN ATG GAQ ACN GAQ GGN CTN CTN TAQ GGN TCN CAP ACN CCN AAQ
                    TTP                             TTP TTP     AGQ 85                              90                          95                          100
Glu Glu Cys Leu Phe Leu Glu Arg Leu Glu Glu Asn His Tyr Asn Thr Tyr Ile Ser Lys
GAP GAP TGQ CTN TTQ CTN GAP CGN CTN GAP GAP AAQ CAQ TAQ AAQ ACN TAQ ATQ TCN AAP
            TTP     TTP     AGP TTP                                     ATA AGQ 105                             110                         115                         120
Lys His Ala Glu Lys His Trp Phe Val Gly Leu Lys Lys Asn Gly Arg Ser Lys Leu Gly
AAP CAQ GCN GAP AAP CAQ TGG TTQ GTN GGN CTN AAP AAP AAQ GGN CGN TCN AAP CTN GGN
                                        TTP                     AGP AGQ     TTP 125                         130                         135                         140
Pro Arg Thr His Phe Gly Gln Lys Ala Ile Leu Phe Leu Pro Leu Pro Val Ser Ser Asp
CCN CGN ACN CAQ TTQ GGN CAP AAP GCN ATQ CTN TTQ CTN CCN CTN CCN GTN TCN TCN GAQ
AGP                                     ATA TTP     TTP     TTP         AGQ AGQ
```

Where Q = C or T,
    P = A or G, and
    N = A, T, C, or G

The bovine gene is constructed with a leader portion containing a single restriction enzyme cleavage site and an N-terminal methionine codon for a translational start site. The gene also contains a tail containing tandem translational stop codons and two restriction enzyme cleavage sites. The redundancy of the genetic code allows a choice of base sequences which in turn allows for the incorporation of unique restriction enzyme cleavage sites throughout the gene. The preferred bovine gene base sequence with the location of the restriction enzyme cleavage sites is shown in the following table:

TABLE VI

```
      1
      Met Phe Asn Leu Pro Leu Gly Asn Tyr Lys Leu Leu Tyr Cys Ser Asn Gly Gly Tyr Phe Leu Arg Ile Leu Pro Asp Gly Thr Val Asp
                                        10                          20                          30
                            [1]                                                            [3]
       1                      20                       40                       60                       80                      100
       AATTCATGTTCAATCTGCCACTGGGTAACTATAAAAAGCCAAAGCTTCT TTACTGCTC TAACGGTGGTTACTTTCTCCGCATCCTGCCAGATGGTACCGTGGAC
                                            [2]                                          [4]
      (EcoRI)                                       HindIII                                                              KpnI Gly Thr Lys Asp Arg Ser Asp Gln His Ile Gln Leu Gln Leu Cys Ala Glu Ser Ile Gly Glu Val Tyr Ile Lys Ser Thr Glu Thr Gly Gln Phe Leu Ala Met
                         40                          50                          60
      GTACAAGTTAGACGGTGACCCATTAAATGTTTTTCGGTTTCGAAGA AATGACGAGATTGCCACCAATGAAAGAGGCGTAGGACGGTCTACCATGGCACCTG
                                                                                              [7]
                         120                       140                         160                          180                          200
      GGCA CCAAAGATCG TTCTGATCAACATATTCAACTGCAGCTGTGCGCCGAATCTATCGGT GAAGTTTAC ATCAAATCTACCGAAACTGGTCAATTCCTTGCCATG
                                        [5]                                                                           [8]
                BclI                                 PstIPvuII                Hinfl                                                NcoI Asp Thr Asp Gly Leu Leu Tyr Gly Ser Gln Thr Pro Asn Glu Glu Cys Leu Phe Leu Glu Arg Leu Glu Glu Asn His Tyr Asn Thr Tyr Ile Ser Lys Lys
                          70                          80                          90                            100                    [11]
                                                                                                                           300
                         220                          240                           260                         280
      GACACTGATGGCCTGCTGTACG GATC CCAGACCCCAAACGAGGAGTGCCTTTTCCTGGAGCGCCTGGAGGAAAA CCATTACAAC ACCTACATCTCTAAAAAG
                                    [6]                                     [9]
                                    BamHI                                                  HaeII Leu Pro Arg Thr His Phe Gly Gln Lys Ala Ile Leu Phe Leu Pro
                                        120                         130
                                                           [13]
      CTGTGACTACCGGACGACATGCCTAG GGTTCTGGGGTTTGCTCCTCACGAAAAGGACCTCCTTTTGGTAATGTTG TGGATGTAGAGATTTTTC
                                                                              [10]

His Ala Glu Lys His Trp Phe Val Gly Leu Leu Lys Asn Gly Arg Ser Lys Leu Gly Pro Arg Thr His Phe Gly Gln Lys Ala Ile Leu Phe Leu Pro
                                 110                                   120
                         320                          340                          360                          380                          400
      CATGCTGAGAAACATTGGTT CGTAGGCC TTAAGAAAAATGGCCGCTCTAAACTGGGCCCCTCGTACTCACTTTG GTCAAAAAGC TATCCTGTTCCTGCCA
                              StuI                                                            [13]
      GTACGACTCTTTGTAACCAA GCATCCGG AATTCTTTTTACCGGGGAGCATGAGTGAAAC CAGTTTTTCG ATAGGACAAGGACGGT
      SphI                                                                   [14]
                           ApaI

Leu Pro Val Ser Ser Asp
                          140
```

TABLE VI-continued

```
                       440
[15]
CTGCCAGTGAGCTCTGACTAATAGATATCG
GACGGTCACTCGAGACTGATTATCTATAGCAGCT
  [16]    SacI       EcoRV   (SalI)
```

The gene sequence for each strand of the double-stranded molecule is randomly divided into 8 nucleotide sequences. The oligonucleotides are constructed with overlapping ends to allow the formation of the double-stranded DNA. The following table contains one of a multitude of oligonucleotide arrangements that is used to produce the bovine aFGF gene.

The bovine gene is assembled in 2 steps: first, the half corresponding to the N-terminal portion of the protein; and second, the C-terminal half. Generally, the oligonucleotides are kinased with T4 polynucleotide kinase in the presence of either ATP or $^{32}$P-labelled ATP. In the first reaction of each step the oligonucleotides which make up one strand of the gene are kinased with the

TABLE VII

OLIGO-1    10          20          30          40          50          58

5' AATTCATGTT CAATCTGCCA CTGGGTAATT ACAAAAAGCC AAAGCTTCTT TACTGCTC 3'

OLIGO-2    10          20          30          40     45

5' AGAAGCTTTG GCTTTTTGTA ATTACCCAGT GGCAGATTGA ACATG 3'

OLIGO-3    10          20          30          40          50          60

5' TAACGGTGGT TACTTTCTCC GCATCCTGCC AGATGGTACC GTGGACGGCA CCAAAGATCG 3'

OLIGO-4    10          20          30          40          50      59

5' TGCCGTCCAC GGTACCATCT GGCAGGATGC GGAGAAAGTA ACCACCGTTA GAGCAGTAA 3'

OLIGO-5    10          20          30          40     46

5' TTCTGATCAA CATATTCAAC TGCAGCTGTG CGCCGAATCT ATCGGT 3'

OLIGO-6    10          20          30          40          50          60    65

5' GTAAACTTCA CCGATAGATT CGGCGCACAG CTGCAGTTGA ATATGTTGAT CAGAACGATC TTTGG 3'

OLIGO-7    10          20          30          40          50          60     67

5' GAAGTTTACA TCAAATCTAC CGAAACTGGT CAATTCCTTG CCATGGACAC TGATGGCCTG CTGTACG 3'

OLIGO-8    10          20          30          40          50      60 62

5' GATCCGTACA GCAGGCCATC AGTGTCCATG GCAAGGAATT GACCAGTTTC GGTAGATTTG AT 3'

OLIGO-9    10          20          30          40       50 52

5' GATCCCAGAC CCCAAACGAG GAGTGCCTTT TCCTGGAGCG CCTGGAGGAA AA 3'

OLIGO-10   10          20          30          40          50          58

5' GTTGTAATGG TTTTCCTCCA GGCGCTCCAG GAAAAGGCAC TCCTCGTTTG GGGTCTGG 3'

OLIGO-11   10          20          30          40     48

5' CCATTACAAC ACCTACATCT CTAAAAAGCA TGCTGAGAAA CATTGGTT 3'

OLIGO-12   10          20          30          40     46

5' GGCCTACGAA CCAATGTTTC TCAGCATGCT TTTTAGAGAT GTAGGT 3'

OLIGO-13   10          20          30          40          50    53

5' CGTAGGCCTT AAGAAAAATG GCCGCTCTAA ACTGGGCCCT CGTACTCACT TTG 3'

OLIGO-14   10          20          39          40          50      55

5' GCTTTTTGAC CAAAGTGAGT ACGAGGGCCC AGTTTAGAGC GGCCATTTTT CTTAA 3'

OLIGO-15   10          20          30          40          50         56

5' GTCAAAAAGC TATCCTGTTC CTGCCACTGC CAGTGAGCTC TGACTAATAG ATATCG 3'

OLIGO-16   10          20          30          40          50

5' TCGACGATAT CTATTAGTCA GAGCTCACTG GCAGTGGCAG GAACAGGATA 3'

The oligonucleotides illustrated in Table VII are presented merely as an example of oligonucleotide subunits and should not be construed as limiting thereto. The composite base sequence showing the overlap and arrangement of the oligonucleotides is illustrated in Table II.

exception of the most 5' oligonucleotide. In the second reaction the oligonucleotides which make up the second strand are kinased, with the exception of the most 5' oligonucleotide. When kinased oligonucleotides are used, about 1% of the added oligonucleotide is $^{32}$P-labelled for later identification of the products. Annealing is carried out in an appropriate buffer, such as one containing but not limited to about 60 mM TRIS, about pH 7.6, about 5 mM dithiothreitol (DTT), about 10 mM MgCl₂, and about 30 μM ATP at about 90° C. for about 4 minutes followed by a rapid transfer to about 60° C. and a slow cooling to about 30° C. Ligation is carried out in an appropriate buffer, such as one containing, but not limited to, about 60 mM TRIS, about pH 7.6, about 10 mM DTT, about 10 mM MgCl₂, about 1 mM ATP, and about 0.03 units T4 DNA ligase at about 20° C. for about 1 and ½ hour.

The ligated oligonucleotides are purified by polyacrylamide gel electrophoresis following ethanol precipitation. The oligonucleotides are redissolved in a buffer containing about 20 μl of about 80% formamide, about 50 mM TRIS-borate, about pH 8.3, about 1 mM ethylenediaminetetraacetic acid (EDTA), about 0.1% (w/v) xylene cyanol, and about 0.1% (w/v) bromophenol blue. Each sample is heated at about 90° C. for about 3 minutes and electrophoresed in about a 10% urea-polyacrylamide gel at about 75 watts for about 5 hours. The 231 base N-terminal bands are removed, combined and eluted at about 4° C. in about 0.5 M ammonium acetate containing about 1 mM EDTA at about pH 8. The 209 base C-terminal bands are treated in the same manner.

The synthetic gene sequences coding for either the N-terminal or the C-terminal portions of the aFGF are incorporated into the pBR322 plasmid. It is especially desired and intended that there be included within the scope of this invention, the use of other plasmids into which the aFGF gene can be incorporated and which will allow the expression of the aFGF gene. Reannealed oligonucleotides, about 300 fmole and about 100 fmole of the recovered 231 base pair N-terminus are each ligated to about 100 fmole of agarose gel-purified about 3.9 kilo base (kb) EcoRI-BamHI pBR322 for the N-terminus. The 209 bp C-terminus is constructed in the same manner using BamHI-SalI pBR322. Ligation is carried out in a buffer containing about 25 mM TRIS, about pH 7.8, about 1 mM DTT, about 10 mM MgCl₂, about 0.4 mM ATP, with about 1 unit of T4 DNA ligase for about 1 hour at about 20° C. Each half-gene ligated vector is used to transform competent bacterial cells, such as *E. coli* RR1 (Bethesda Research Laboratories, BRL) following suppliers procedures. The transformed cells are selected for growth in ampicillin and screened for the presence of either the 231 base pair (bp) EcoRI-BamHI insert or the 209 bp BamHI-SalI insert by restriction analysis of mini-lysate plasmid preparations.

The DNA sequence of clones containing the appropriate sized inserts is determined using Maxam and Gilbert, Proc. Natl. Acad. Sci. USA 74: 560–564 (1977) chemical DNA sequence techniques.

The final full-length aFGF synthetic gene was cloned by cleaving the N-terminal half clone with restriction enzymes BamHI and SalI, treating with alkaline phosphatase and ligating this to the gel purified 209 bp BamHI-SalI insert of the C-terminal half clone. This ligated material was used to transform competent RR1 cells as before.

Expression of the synthetic aFGF gene is accomplished by a number of different promoter-expression systems. It is desired and intended that there be included within the scope of this invention, the use of other promoter-expression systems for the expression of the intact aFGF gene. The preferred construct uses the *E. coli* tac promoter, a hybrid between regions of the trp promoter and the lac promoter as described by deBoer et al., Proc. Nat. Acad. Sci. USA 80: 21–25 (1983). Plasmid pKK223-3 (Pharmacia) which contains the tac promoter and rrnB rRNA transcription terminator was modified to remove the pBR322-derived SalI restriction enzyme site. The rrnB rRNA terminator has been shown to allow expression by strong promoters, Gentz et al., Proc. Natl. Acad. Sci. USA 78: 4936–4940 (1981); Brosius, Gene 27: 161–172 (1984).

The pKK223-3 plasmid DNA is cleaved with restriction enzymes to produce a 2.7 kb DNA fragment to generate clone pKK2.7. The synthetic aFGF gene is cleaved from its pBR322 vector and transferred to the pKK2.7 plasmid after restricting pKK2.7 with EcoRI and SalI. The resulting recombinant, shown in FIG. 1, is transformed into *E. coli* JM105 (Pharmacia) or DH5 (BRL) cells and expressed.

Site specific mutagenesis is an efficient way to convert the amino acid sequence of one mammalian species of aFGF to the aFGF amino acid sequence of another species. The following description relates to the site specific mutagenic conversion of bovine aFGF, 140 amino acid form (numbered in accordance with the native form), to human aFGF, it is to be understood, however, that the process can be used to convert any mammalian species aFGF to that of any other species. The only limitation on the conversion is that the amino acid sequences of both aFGFs must be known. The following table lists the amino acids which must be substituted and the location on the bovine aFGF amino acid map, Table VI, at which the substitutions are made:

TABLE VIII

| Amino Acid | Substituted Amino Acids | |
| Location | Human aFGF | for Bovine aFGF |
| --- | --- | --- |
| 5 | Pro | Leu |
| 21 | His | Tyr |
| 35 | Arg | Lys |
| 47 | Ser | Cys |
| 51 | Val | Ile |
| 64 | Tyr | Phe |
| 106 | Asn | His |
| 116 | Ser | Arg |
| 117 | Cys | Ser |
| 119 | Arg | Leu |
| 125 | Tyr | Phe |

As with the bovine gene sequence eight oligonucleotides representing the human gene sequence are constructed by the same procedure as that used for the bovine oligonucleotides. The following table contains one of a multitude of oligonucleotide arrangements that is used to produce the human aFGF gene.

TABLE IX

OLIGO-1

5' CTGCCACCGGGTAATTAC 3'

OLIGO-2

5' CGGTGGTCACTTTCTCCG 3'

OLIGO-3

5' CGGCACCAGAGATCGTTC 3'

OLIGO-4

5' GCAGCTGTCCGCCGAATCTGTCGGTGAAG 3'

TABLE IX-continued

OLIGO-5

5' CTGGTCAATACCTTGCCATGG 3'

OLIGO-6

5' GCTGAGAAAAATTGGTTCG 3'

OLIGO-7

5' GGCCGCGTTTACAGCTGCCATTTTTCTTAAGG 3'

OLIGO-8

5' CGTACTCACTATGGCCAAAAAGCTATCC 3'

The cloned synthetic bovine gene for aFGF is converted to a human synthetic gene for aFGF by a series of directed point mutations. Oligonucleotide-directed mutagenesis of the cloned gene allows the alteration of the base sequence of bovine aFGF so that the resulting amino acid sequence contains the substituted amino acids shown in Table VIII and is human aFGF. A deletion is made in the bovine gene to remove the amino terminal phenylalanine for the production of the human 139 amino acid microheterogeneous form of aFGF. A point mutation is carried out to replace the second position asparagine with aspartic acid. Alternatively, the asparagine is deamidated to aspartic acid. The methods for carrying out these procedures are described below or are known in the art. The oligonucleotide-directed mutagenesis is carried out using standard procedures known to the art, Zoller and Smith, Methods in Enzymology, 100: 468–500 (1983); Norris et al., Nucleic Acids Research, 11: 5103–5112 (1983); and Zoller and Smith, DNA, 3: 479–488 (1984). The point mutations of the bovine to human conversion are carried out by the standardized oligonucleotide-directed mutagenesis and are shown in the following Table. The location of the base mutagenesis can be seen in Table X.

TABLE X

| Base Location | Substituted Base Human aFGF | for Bovine aFGF | Corresponding Human Amino Acid |
|---|---|---|---|
| 22 | C | T | Pro |
| 69 | C | T | His |
| 112 | G | A | Arg |
| 148 | C | G | Ser |
| 159 | G | A | Val |
| 199 | A | T | Tyr |
| 324 | A | C | Asn |
| 354 | A | C | Ser |
| 358 | G | C | Cys |
| 364 | G | T | Arg |
| 365 | C | G | Arg |
| 382 | A | T | Tyr |

To expedite the mutagenesis of the bovine aFGF gene it is transfered to a standard vector, M13mp19, a single-stranded DNA bacteriophage vector. The bovine pKK-aFGF plasmid is cleaved with EcoRI and SalI and the resulting 440 bp fragment is gel purified. Vector M13mp19 RF DNA is cleaved with the same two endonucleases and the ends are subsequently dephosphorylated with bacterial alkaline phosphatase. The vector DNA and the aFGF gene fragment DNA are ligated and the mixture is used to transform E. coli DH5 cells. A phage clone containing the bovine aFGF gene is selected, M13mp19-baFGF.

The human oligomers shown in Table IX are phosphorylated and annealed individually to M13mp19-baFGF single-stranded phage DNA. Closed-circular double-stranded molecules are prepared with T4 DNA ligase and DNA polymerase I klenow fragment. The preparations were each used to transform competent JM105 cells and the resulting transformant plaques are selected by hybridization with the appropriate oligomer which is labeled using polynucleotide kinase. Single-stranded DNA is isolated from the phage clone containing the human oligmer 4 mutations and the above procedure is repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Volumes of each fragment are collectively ligated to a gel-purified 3.7 kb EcoRI-SalI fragment from pBR322 with T4 DNA ligase and used to transform competent E. coli DH5 cells (BRL) as described by the supplier. A clone containing the mutations specified by all four mutant oligomers is selected by hybridization with radiolabeled probes prepared from each of the oligomers. The 140 bp KpnI-BamHI DNA fragment isolated from cleaved RF DNA of the human 3 mutant M13 clone is ligated to endonuclease cleavage products of this human 1-2-6-8 mutant DNA and transformed into DH5 competent cells to generate a clone with the human 1-2-3-6-8 mutations. BamHI-PstI digestion fragments of this latter clone are ligated to the BamHI-PstI digestion fragments of RF DNA from the human 4-5 M13-based clone and the ligation mixture is used to transform DH5 competent cells. A clone containing the human 1-2-3-4-5-6-8 mutations is selected by oligomer hybridization and the aFGF gene EcoRI-SalI DNA fragment of this recombinant plasmid is ligated to phosphatase-treated EcoRI-SalI-cleaved RF DNA of M13mp18 (BRL). Competent DH5 cells are transformed with this ligated DNA and the transformed cells are plated on JM105 host cells to generate an M13 clone. The single-stranded phage DNA of this clone was annealed with the human 7 oligomer and an M13 clone containing all the desired mutations was obtained following the procedure described above. The human aFGF clone is designated M13mp18-haFGF.

Pure aFGF in the absence of heparin becomes less active presumably due to the generation of incorrectly stabilized intramolecular disulfide bonds and aggregates formed by intermolecular disulfide bonds. The covalent disulfide bonds are formed between two cysteine residues either in two separate polypeptide chains, interchain disulfide bond, or in different positions within a single chain, intrachain disulfide bond. In the case of enzymatic oxidative iodination, the active molecules can be recovered by reduction with 20 mM dithiothreitol in the presence of 3 M guanidinium chloride at a pH of about 9.1. The present invention utilizes site-directed mutagenesis for the specific substitution or deletion of amino acids capable of forming extraneous intramolecular or intermolecular covalent bonds and oxidation susceptable amino acids. Substitution as used herein refers to a deliberate change in the DNA base sequence of aFGF such that a desired amino acid is substituted for an undesired amino acid. The undesired amino acid may be one which forms unwanted covalent bonds, especially disulfide bonds, or one which is air-oxidizable either of which may decrease the biological activity of the molecule. A deletion as used herein refers to a deliberate change in the DNA base sequence of aFGF resulting in the elimination of the unwanted amino acid. The primary amino acid associated with intramolecular and intermolecular covalent bond formation is cysteine while the amino acids which are oxidization prone include cysteine, methionine and tryptophan. The cysteine residue or residues may be replaced with any amino acid which will not form disulfide bonds. The prefered amino acid for the substitution of cysteine is serine. The oxidation prone amino acids are replaced with any amino acid which is oxidation resistant, this includes, but is not restricted to, alanine, valine, leucine and isoleucine.

The invention is contemplated to include site-specific mutations of one or more of the cysteine residues and any non-terminal methionine residue which could render native or recombinant aFGF less active or inactive due to the formation of incorrect intramolecular or intermolecular bonds or oxidative changes. The recombinant and native human and bovine protein contains two cysteine residues in common located at positions 16 and 83 and a methionine residue in common located at position 67 as defined by the native 140 amino acid form of both bovine and human aFGF. Bovine and human aFGFs each contain a third cysteine residue at positions 47 and 117, respectively. The common cysteine residues are the most likely to form a disulfide bond since the location of cysteine residues in disulfide bonds is highly conserved in homologous proteins. Thus the third cysteine residues that are in different locations in bovine and human aFGFs are very likely not found in disulfide linkages in the fully active proteins. It will be understood that the novel mutant aFGFs of the present invention will not only include the forms substituted at the non-common cysteine residues but also those that have all cysteines substituted or deleted, those in which any one or two of the cysteines have been substituted or deleted and those in which methionine has been substituted or deleted. The substitution or deletion of any one, especially the unique cysteine, all cysteines, two of the three cysteines or methionine in the human or bovine aFGF by site-directed mutagenesis may after the formation of unwanted intramolecular and intermolecular disulfide bonds and oxidized forms.

Site-specific mutagenesis is carried out on preferably bovine or human r-aFGF produced from genomic DNA, cDNA or by construction of genes for one or more of the microheterogeneous forms of the protein based on the microheterogeneous forms of aFGF from mammalian species including man. Genomic DNA is extracted from mammalian brain or pituitary cells and prepared for cloning by either random fragmentation of high molecular weight DNA following the technique of Maniatis et al., Cell 15: 687–701 (1978) or by cleavage with a restriction enzyme by the method of Smithies et al., Science 202: 1284–1289 (1978). The genomic DNA is then incorporated into an appropriate cloning vector, generally E. coli lambda phage, see Maniatis et al., Molecular Cloning, A Laboratory Manual, Cold Spring Harbor Laboratory, Cold Spring Harbor, N.Y. (1982).

To obtain cDNA for aFGF, poly (A)-containing RNA is extracted from cells that express aFGF by the method of Aviv and Leder, Proc. Natl. Acad. Sci. 69: 1408–1412 (1972). The cDNA is prepared using reverse transcriptase and DNA polymerase using standard techniques, as described in Maniatis et al., Molecular Cloning, a Laboratory Manual, Cold Spring Harbor Laboratory, Cold Spring Harbor, N.Y. (1982). The cDNA is tailed and cloned into an appropriate vector, usually pBR322, by a technique similar to that of Wensink, et al., Cell 3: 315–325 (1974).

The clonal genomic DNA or cDNA libraries are screened to identify the clones containing aFGF sequences by hybridization with an oligonucleotide probe. The sequence of the oligonucleotide hybridization probe is based on the determined amino acid sequence of aFGF. Maniatis et al., supra, Anderson and Kingston, Proc. Natl. Acad. Sci. USA 80: 6838–6842 (1983) and Suggs et al., Proc. Natl. Acad. Sci. USA 78: 6613–6617 (1981) describe various procedures for screening genomic and cDNA clones. The preferred procedure is to specifically point mutate the synthesized bovine and human genes as described above.

Site-specific mutagenesis is carried out on a human or bovine aFGF single-stranded bacteriophage recombinant clone, such as M13mp18-haFGF or M13mp19-baFGF following the procedures of Zoller, and Smith, Methods in Enzym. 100: 468–500 (1983), Norris et al., Nucleic Acids Res. 11: 5103–5112 (1983), and Zoller and Smith, DNA 3: 479–488 (1984). Three oligonucleotides for each species are designed to specify serine codons in place of each of the cysteine codons of the human aFGF gene at positions 16, 83 and 117 and at positions 16, 47 and 83 for the bovine gene. An oligonucleotide is designed to specify a leucine codon in place of the methionine codon of the human or bovine aFGF at position 67. The human oligomers synthesized are shown in the following table with the mutated bases underlined.

TABLE XI

Cysteine 1 (16) 5' CCGTT AGAGGAGT AAAGAAGC 3'

Cysteine 2 (83) 5' GGAAAAGGGACTCCTCG 3'

Cysteine 3 (117) 5' CCGCGTTTAGAGCTGCC 3'

Methionine (67) 5' CCATCAGTGTCCAGGGCAAGG 3'

Similar oligomers are identified for the appropriate regions of the bovine aFGF gene and the specific mutations carried out as described below.

The human oligomers are phosphorylated and annealed individually to M13mp18-haFGF or M13mp19-baFGF single-stranded DNA. A second strand of DNA is synthesized using the annealed oligomer as primer. Each cysteine mutated gene is used to transform an appropriate host such as competent E. coli DH5 cells.

The transformed cells are plated on a lawn of an acceptable host for the M13 virus such as *E. coli* JM105 cells. The transformed plaques are selected by hybridization with the appropriately labeled oligomer. Conditions of hybridization are optimized for each probe to prevent retention of hybrids containing single base changes. Single-stranded DNA is isolated from phage clones containing each of the cysteine-to-serine mutations for DNA sequence analysis using the method of Sanger et al., Proc. Natl. Acad. Sci. USA 74: 5463-5467 (1977). RF DNAs are prepared for each clone, cleaved with EcoRI and SalI and purified by agarose gel electrophoresis. The purified 440 bp inserts are individually ligated to the 2.7 kb EcoRI-SalI DNA fragment of the pKK2.7 tac promoter expression vector. The ligated DNAs are used to transform competent DH5 cells and clones containing DNA with the mutated cysteine codons are selected by hybridization to the appropriate oligomer. Each aFGF gene insert is sequenced by the method of Maxam and Gilbert, Methods in Enzymololgy 65: 499-560 (1980). The clones containing the single base change from the original human DNA are designated: pKK-haFGF (Ser 16), pKK-haFGF (Ser 83) and pKK-haFGF (Ser 117); while the bovine DNA; is designated pKK-baFGF (Ser 16), pKK-baFGF (Ser 47) and pKK-baFGF (Ser 83), for the location of the substitution in the protein.

Substitution of any two or all three of the cysteine residues is accomplished by multiple point mutations or by combining restriction fragments of either human-or bovine-recombinant wild-type and the (Ser 16), (Ser 47), (Ser 83) and (Ser 117) mutant synthetic genes, cloned in M13mp19 for bovine and M13mp18 for human, and subcloned in pKK2.7 as described above. It is to be understood that the multiple mutations can be carried out with either the bovine or human single mutation aFGF constructs as described above, however, the following illustration will include only human aFGF. The pKK-haFGF (Ser 16,32) and pKK-haFGF (Ser 16,32) recombinants are constructed by introducing the 0.23 Kb EcoR1-BamH1 fragment of M13mp18 (Ser 16) into pKK2.7 followed by insertion of the 0.2 Kb BamH1-SalI fragments either from M13mp18 (Ser 83) or from M13mp18 (Ser 117). The pKK2.7 vector is modified to remove the BamH1 site upstream of the tac promoter while leaving the BamH1 site in the multicloning sequence. Following digestion with the corresponding restriction enzymes, subsequent ligation and transformation of an appropriate host, clones are selected and screened for those containing plasmids with the expected molecular weight for the recombinants, about 3.1Kb. An appropriate bacterial host may include, but is not limited to, *E. coli* DH5, JM105 or AB1899.

The mutant haFGF (Ser 16,83,117) is constructed by replacing the 0.13 Kb Sph1-SalI fragment of pKK-haFGF (Ser 16,83), by the corresponding fragment of pKK-haFGF (Ser 117) that encodes for Ser instead of Cys in the 117 position. The 3 Kb Sph1-SalI fragment of pKK-haFGF (Ser 16,83) is purified by preparative agarose gel electrophoresis, electroelution and ligated to the 0.13 Kb Sph1-SalI fragment of pKK-haFGF (Ser 117) purified from a 5% polyacrylamide gel in the same way. The purified fragments are ligated and recombinants selected as described above.

The pKK-haFGF (Ser 83,117) mutant is constructed by replacing the 0.3 Kb PstI fragment of pKK-haFGF, the non-mutated form, with the fragment pKK-haFGF (Ser 16,83,117) that includes the codons for Ser instead of Cys at positions 83 and 117 using the above techniques. Transformants are analyzed by PstI-SalI digestion to determine the orientation of the ligated fragments. All genes are sequenced by the dideoxy method of Sanger et al., Proc. Natl. Acad. Sci. USA 74: 5463-5467 (1977).

Expression of a mutated aFGF gene is accomplished by a number of different promoter-expression systems in a number of different host cells. It is desired and intended that there be included within the scope of this invention, the use of other host cells and promoter-expression systems for the expression of the intact mutated aFGF gene. The host cells include bacteria, yeast, insect, and mammalian cells. The antigens may also be expressed in viruses. Although the genes can be expressed in numerous procaryotic cells and various eucaryotic cells the preferred host cell is *Escherichia coli*. The expression vectors which can be used for the expression of the mutated aFGF include, but are not limited to, pBR322, pPLa2311, pKC30, ptac12, λgt11, CheY, pAS1, pLC24, pSB226, SV40 and pKK223-3 with pKK223-3 being preferred. *Escherichia coli* expression vectors generally allow the translation of a methionine residue attached to the first amino acid of the desired protein. It will be understood that the present invention includes not only mutant r-aFGF with a terminal methionine but also mutant r-aFGF which has had the terminal methionine removed following translation in such cell types as yeast cells, mammalian cells or bacterial cells. The expression vector may have included in the DNA sequence one or more additional cistrons which will enhance the expression of the aFGF gene, Schoner et al., Proc. Natl. Acad. Sci USA 83: 8506-8510 (1986). The preferred construct uses the *E. coli* tac promoter, a hybrid between regions of the trp promoter and the lac promoter as described by deBoer et al., Proc. Nat. Acad. Sci. USA 80: 21-25 (1983). Plasmid pKK 223-3 (Pharmacia) which contains the tac promoter and rrnB rRNA transcription terminator was modified to remove the pBR322-derived SalI restriction enzyme site. The rrnB rRNA terminator has been shown to allow expression by strong promoters, Gentz et al., Proc. Natl. Acad. Sci. USA 78: 4936-4940 (1981); Brosius, Gene 27: 161-172 (1984).

The pKK223-3 plasmid DNA is cleaved with restriction enzymes to produce a 2.7 kb DNA fragment to generate clone pKK2.7. The synthetic aFGF gene is cleaved from its pBR322 vector and transferred to the pKK2.7 plasmid after restricting pKK2.7 with EcoRI and SalI. The resulting recombinant, shown in FIG. 1, is transformed into *E. coli* JM105 (Pharmacia) or DH5 (BRL) cells and expressed.

The preferred enhancing expression vector will contain a nucleotide sequence, the first cistron, upstream of the gene encoding the desired protein, the second cistron. The mutated aFGF will be the second cistron. The first cistron will generally contain a Shine-Dalgarno sequence upstream of the stop codon. An enhancing expression vector may contain, but is not limited to, the following nucleotide sequence:

AATTATGTATCGATTAAATAAGGAGGAAT

TACATAGCTAATTTATTCCTCCTTATTAA (pKK2.7)   (cistron 1,2 oligomers)   (aFGF)

which is an effective first cistron for enhancing the expression of wild-type or mutant aFGF. The first cistron is inserted into the appropriate pKK-haFGF construct at the EcoR1 site. The insertion results in the loss of the EcoR1 cloning site. The recombinant is transformed into an appropriate host cell such as those described above and expressed. This construct results in about a 10-fold increase in wild-type or mutant aFGF expression. The plasmids containing the enhancing expression vector are designated pKK2c-haFGF. The present invention is contemplated to include clones containing the enhancing expression vector such as; pKK2c-haFGF (Ser 16), pKK2c-haFGF (Ser 83), pKK2c-haFGF (Ser 117), pKK2c-haFGF (Ser 16,83), pKK2c-haFGF (Ser 16,117), pKK2c-haFGF (Ser 83,117), pKK2c-haFGF (Ser 16,83,117).

The mutated expression clones are grown at about 37° C. in an appropriate growth medium, which consists of about 1% tryptone, about 0.5% yeast extract, about 0.5% NaCl, about 0.4% glucose and about 50 μg/ml ampicillin. When the optical density at 550 nm reaches about 0.5, isopropyl-β-D-thiogatactopyranoside (IPTG) may be added to give a final concentration of about 1 mM and growth is continued at about 37° C. for up to about 24 hours. The cells from 1 liter of culture medium are harvested by centrifugation and resuspended in a washing buffer containing about 100 mM phosphate and about 5 mg/ml EDTA. After the final resuspension about 0.1 mg/ml of lysozyme is added and the suspension is incubated with gentle shaking at about 30° C. for about 15 minutes. The cells are collected by centrifugation and resuspended in a disruption buffer containing about 100 mM sodium phosphate at about pH 6.0, about 3 mM EDTA, about 0.03 mM N-p-toluenesulfonyl-L-phenyl-alanine chloromethyl ketone (TPCK), about 0.05mM pepstatin A, about 0.05 mM phenylmethylsulfonyl fluoride (PMSF), about 0.05mM leupeptin and about 15 μg/ml bovine pancreatic trypsin inhibitor (BPTI). The cells are either immediately disrupted or frozen and stored at −70° C. and disrupted immediately after thawing by about two passages through a French pressure cell at about 20,000 psi at about 4° C. The supernatant fluid is collected following centrifugation and lyophilyzed.

The mutated aFGFs are purified to homogeneity by a three step chromatography process employing a cation exchanger matrix followed by a Heparin-Sepharose affinity matrix followed by reverse phase high performance liquid chromatography (HPLC). The lyophilyzed supernatant fluids are resuspended in phosphate buffer, about 100 mM, about pH 6.0 and added to a cation exchanger, preferably CM-Sephadex which has been equilibrated with the same buffer. The CM-Sephadex is added at a ratio of about 6.5 ml of settled resin per gram of protein. The resin is collected in a scintered glass funnel and washed three times with phosphate buffered saline, about 100mM phosphate and about 150 mM NaCl at a pH of about 6. The resin is resuspended in the same buffer, packed in a column, washed and eluted with about 600 mM NaCl buffer. Heparin-Sepharose is equilibrated with about 10 mM phosphate buffer, pH about 7.2 added to the eluate at a ratio of about 1 ml of settled resin per 1 mg of protein, gently shaken for about 1 hour at about 4° and the resin-protein complex collected in a funnel. The resin is resuspended in the same buffer and packed in a column at 1–2 column volume per hour. The column was washed with a buffer containing about 10 mM phosphate, pH about 7.2 and about 0.8 M NaCl and eluted with 1.5 M NaCl in the same buffer. Each protein was collected and further purified by reverse phase HPLC. Fractions are loaded on an HPLC reversed phase column, about $C_3$, equilibrated with about 10 mM trifluoroacetic acid (TFA) and eluted with a gradient of from about 0 to about 100% 4 mM TFA, about 0–67% $CH_3CN$ in about 30 minutes.

Mitogenic activity of the purified mutated recombinant aFGFs is determined by incorporation of $^3H$-thymidine into DNA by cell line fibroblasts, preferably BALB/c 3T3 A31 (American Type Culture Collection). Mutant proteins from plasmids pKK-haFGF (Ser 16) and pKK-haFGF (Ser 83) stimulated fibroblasts at a level equal to or lower than the non-mutated human aFGF. Mutant protein pKK-haFGF (Ser 117) showed a stimulatory activity that is higher than the non-mutated forms in the absence of heparin.

A well controlled and very reproducible mitogenic assay is required to compare the relative specific mitogenic activities of wild-type haFGF and the Cys to Ser mutants. Confluent cultures of Balb/c 3T3 cells in serum free culture fluid were stimulated with consecutive two-fold dilutions over at least 3 log orders of aFGF concentration spanning the complete rise of the response from background through peak DNA synthesis. One stimulatory unit is calculated as the amount of aFGF per ml that generated a half maximal response. The specific mitogenic activity is the number of stimulatory units per mg of pure aFGF. The assay is further standardized by diluting stock solutions to about 50 μg aFGF/ml of $TFA/CH_3CN$, or less. The dilution eliminates any concentration effect so that different samples can be compared.

Conversion of the Cys 117, any two Cys or all three Cys residues to Ser results in a 7 to 20 fold increase of the specific activity of the protein in the absence of heparin. Even in the presence of heparin, all 4 multiple mutants are are more active than wild-type human r-aFGF with haFGF (Ser 83,117) being about 2.7-fold more active. Although heparin stimulates the activity of wild-type aFGF 20-fold, it potentiates the activity of the mutants by only about 3- to about 5-fold.

Conversion of either all, or of any two, of the three Cys residues of human aFGF to Ser results in a 7 to 20 fold increase of the specific activity of the protein in the absence of heparin. Even in the presence of heparin, all four multiple mutants are more active than non-mutated haFGF, with haFGF Ser (83,117) being nearly 3-fold more active.

Mutated recombinant aFGF is useful in promoting the repair or healing of, but not limited to, soft tissue wounds resulting from burns, cuts or lacerations, and cutaneous ulcerations along with musculo-skeletal wounds such as bone fractures, ligament and tendon tears, and inflammation of bursas and tendons. Tissue repair as used herein is defined as the regeneration of tissue following the stimulation of mesodermal, ectodermal or neuroectodermal derived cells by aFGF. Mutated r-aFGF is also useful in promoting the healing and regeneration of cartilage and cartilageneous tissue. Administration of mutated aFGF for soft tissue repair, including corneal tissue, will generally be by topical, subcutaneous, intravenous or intraocular application. Soft tissue includes all tissue except that associated with the musculo-skeletal system as described above. The novel peptides may be administered with or without heparin, preferably without heparin, about 0.1 to about 100 μg/cm²/day of this invention, protein, to the wound area either topically or subcutaneously about 1 to about 100 μg/cm³/day. The most preferred application range for topical administration is about 1 to about 10 μg/cm²/day.

Heparin is a sulfated glycosaminoglycan consisting of equal parts of the sugars D-glucosamine and D-glucuronic acid which are sulfated to varying degrees. It is commercially available in an unmodified form as well as in a solution form for direct therapeutic utilization. When heparin is administered with aFGF in topical or subcutaneous applications the preferred concentration is from about 3 times to about 30 times the amount (mass) of aFGF administered per day.

For musculo-skeletal and cartilage repair or healing, the mutated r-aFGF is preferably administered at the site of the injury either during surgery or by injection. Surgical implantation of slow-release forms of the mutated aFGF will allow for a continued release of the growth factor for a prolonged period of time. Methods of formulation of mutated aFGF for slow release are known in the art. Dosage levels for musculo-skeletal healing will be about 10 to about 100 μg/cm³/day.

Mutant r-aFGF is furthermore useful in promoting the facilitation of in vivo vascular tissue repair, such as blood vessel growth (angiogenesis), and vessel repair (such as the replacement of damaged endothelial cells) and in stimulating endothelial cell growth on appropriate substrates for the production of blood vessels for implantation. In vivo angiogenesis activity of the novel mutant r-aFGF peptides is accomplished by the internal administistion, such as subcutaneously, of about 1 to 1000 μg/cm³/day with the more preferred amount of about 10 to about 100 μg/cm²/day. The preferred application range for surface repair is about 100 ng to about 100 μg/cm²/day with the most preferred application range being about 1 to about 10 μg/cm²/day. Large vessel repair is accomplished by a single dose of about 0.1 to about 100 ng/cm³ or by continuous infusion of about 1 to about 1000 pg/cm³/day. In vitro growth of Endothelial cells on appropriate substrates for the production of blood vessels is accomplished by the administration of about 1 to about 10 ng/ml/day.

Mutant r-aFGF is also useful in the in vivo induction of plasminogen activator by vascular endothelial cells for the treatment of thrombotic attacks. Thrombotic attacks result form the formation of thrombi within blood vessels which may result in thrombotic strokes, deep vein thrombosis, myocardial infarction and other medical conditions which give rise to necrosis of tissues and often times death of the patient. Digestion of preformed clots and the prevention of further clot formation can be mediated by mutant r-aFGF thereby enhancing the treatment of thrombotic attacks. Pretreatment with mutant r-aFGF may also be used to prevent the formation of clots in animals, including man, which are at high risk for clot formation. The desirable dosage range of mutant r-aFGF for the treatment of thrombotic attack is about 10 μg-10 mg/kg/day.

Mutated and wild-type r-aFGF is also useful in promoting central and peripheral nerve tissue repair including the maintenance and stimulation of hippocampal neurons and neurons that are damaged or destroyed in Alzheimer's disease and motor and sensory neurons whose destruction causes paralysis. Damaged nervous tissue may be stimulated by mutated or wild-type aFGF to produce additional neurons by mitosis of neuroblasts to re-populate the damaged nerves in the area and to promote neurite outgrowth from neurons. The peptides may be administered as described for wound healing of either soft tissue or musculo-skeletal tissue.

For topical application, various pharmaceutical formulations are useful for the administration of the active compound of this invention. Such formulations include, but are not limited to the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxyalkyl celluloses and alkylhydroxyalkyl celluloses, for example methylcellulose, hydroxyethyl cellulose, carboxymethyl cellulose, hydroxypropyl methylcellulose, and hydroxypropyl cellulose; poloxamers such as Pluronic ® Polyols exemplified by Pluronic F-127; tetronics such as tetronic 1508; and alginates such as sodium aliginate. The pharmaceutical formulations will include one or more of the mutated aFGF compounds in amounts of about 0.1 to about 100 μg/ml.

For non-topical application the mutant r-aFGF is administered in combination with pharmaceutically acceptable carriers or diluents such as, phosphate buffer, saline, phosphate buffered saline, Ringer's solution, and the like, in a pharmaceutical composition, according to standard pharmaceutical practice.

The ability of mutated aFGF to stimulate division in various cell types including fibroblasts, vascular and corneal endothelial cells and the like makes these peptides useful as pharmaceutical agents. These compounds can be used to treat wounds of mammals including humans by the administration of the novel mutated r-aFGF to patients in need of such treatment.

The following examples illustrate the present invention without, however, limiting the same thereto.

EXAMPLE 1

Oligonucleotide Synthesis

Oligonucleotides were synthesized according to the technique described by Matteucci and Caruthers, J. Am. Chem. Soc. 103: 3185–3191 (1981); Beaucage and Caruthers, Tetrahedron Letters 22: 1859–1862 (1981). The base sequences of the synthesized oligonucleotides are shown in Tables VII, IX and XI.

EXAMPLE 2

Assembly of the aFGF Gene

The bovine oligonucleotides from Example 1 were assembled as two separate units, the N-terminal half (231 bp) and the C-terminal half (209 bp). The two halves were then combined for the intact synthetic gene, see Table VI. Initially the oligonucleotides were kinased in the following reaction mixture: 70 mM Tris pH 7.6, 5 mM DTT, 10 mM MgCl$_2$, 33 μM ATP, 0.3 units T4 polynucleotide kinase per μl, and 2.5 pmole oligonucleotide per μl. The mixture was incubated 1.5 hours at 37° C. and then an additional hour after supplementing the mixture with 0.2 units/μl kinase and ATP to give a concentration of 100 mM. For radioactive labelling, the initial mixture contained 37 nCi/μl of [γ-$^{32}$P]-ATP.

The annealing and ligations were done in two separate reactions. In each reaction, 100 pmole of each of the eight oligonucleotides were added. In one reaction the oligonucleotides which make up one strand of the C-terminal or N-terminal half gene were kinased with the exception of the most 5' oligonucleotide. In the second reaction the oligonucleotides which make up the opposite strand were kinased, again with the exception of the most 5' oligonucleotide. Thus, in each reaction 3 oligonucleotides were kinased and 5 were not. When kinased oligonucleotides were used, 1 pmole of the $^{32}$P-labelled oligonucleotide was also added for later identification of the products. Each reaction contained 200 µl with 70 mM Tris pH 7.6, 5 mM DTT, 10 mM MgCl$_2$, and 30 µM ATP. The oligonucleotides were annealed by heating to 90° C. for 4 minutes, then immediately transferring the reaction to 60° C. and allowing it to cool slowly to 30° C. Ligation was done in 400 µl containing 60 mM Tris pH 7.6, 10 mM DTT, 10 mM MgCl$_2$, mM ATP, and 0.03 units T4 DNA ligase per µl by incubating at 20° C. for 1.5 hours.

Polyacrylamide gel electrophoresis was used to purify the ligated oligonucleotides. The ligated oligonucleotides were precipitated with ethanol, redissolved in 20 µl of 80% formamide, 50 mM TRIS-borate pH 8.3, 1 mM EDTA, 0.1% (w/v) xylene cyanol, and 0.1% (w/v) bromophenol blue. Each sample was heated at 90° C. for 3 minutes and electrophoresed in a 10% urea-polyacrylamide gel at 75 watts for 5 hours. The oligonucleotide bands were visualized by exposing the gel to X-ray film.

The 231 base bands of each reaction for the N-terminus were cut out of the gel, combined, and eluted at 4° C. in 1 ml of 0.5 M ammonium acetate, 1 mM EDTA pH 8. The eluted DNA was precipitated with ethanol and redissolved in 30 µl of 70 mM Tris pH 7.6, 5 mM DTT, and 10 mM MgCl$_2$. The 209 base bands of the C-terminus were eluted in the same manner.

The gel purified oligonucleotides were annealed prior to transformation by heating to 90° C. for 4 minutes and slow cooling to 20° C. Assuming a 5% recovery from the initial starting oligonucleotides, 300 fmole and 100 fmole of recovered annealed 231 bp oligonucleotides were each ligated to 100 fmole of agarose gel purified 3.9.kb EcoRI-BamHI pBR322 fragment DNA in 20 µl of 25 mM Tris pH 7.8, 1 mM DTT, 10 mM MgCl$_2$, 0.4 mM ATP, with 1 unit T4 DNA ligase for 1 hour at 20° C. The annealed 209 bp oligonucleotides were ligated to agarose purified 3.9 kb BamHI-SalI pBR322 fragment DNA under the same conditions as the 231 base pair fragments. The ligation reactions were diluted 1:5 in H$_2$O and 1 µl of dilution was used to transform 20 µl of competent *E. coli* RR1 cells (BRL) as described by the supplier. The transformants were selected for growth in ampicillin and screened for the presence of the 231 bp EcoRI-BamHI or the 209 bp BamHI-SalI insert by restriction analysis of mini-lysate plasmid preparations.

The DNA sequence of clones containing the appropriate sized inserts was determined using the chemical DNA sequence techniques of Maxam and Gilbert, Proc. Natl. Acad. Sci. USA 74: 560–564 (1977). Since none of the 231 bp clones had the correct sequence, a clone containing the correct sequence was prepared as follows. One clone with the correct sequence between the KpnI and BamHI sites was cleaved with KpnI and with SalI, which cleaves in the pBR322 vector. The 400 bp band was gel purified and ligated to the 3.8 kb KpnI-SalI band of a second clone containing the correct sequence from the EcoRI site to the KpnI site of the aFGF gene insert. After transformation, a resulting clone was sequenced to ensure the desired sequence had been obtained.

Since a clone containing the correct 209 bp sequence was obtained, no further manipulation of these clones was required. The final full-length aFGF synthetic gene was cloned by cleaving the N-terminal half clone with BamHI and SalI, treating with alkaline phosphatase, and ligating this to the gel purified 209 bp BamHI-SalI insert of the C-terminal half clone. This ligated material was used to transform competent RR1 cells as before.

EXAMPLE 3

Mutagenesis of the Bovine aFGF Gene to the Human aFGF Gene

To facilitate the mutagenesis of the bovine aFGF gene, the synthetic gene from Example 2 was transferred to M13mp19, a single-stranded DNA bacteriophage vector. Standard mutagenesis procedures were used as reported by Zoller and Smith, Methods in Enzymology, 100: 468–500 (1983); Norris et al., Nucleic Acids Research, 11: 5103–5112 (1983); and Zoller and Smith, DNA, 3: 479–488 (1984). The bovine pKK-aFGF plasmid was cleaved with EcoRI and SalI and the resulting 440 bp fragment was agarose gel purified as in Example 2. Vector M13mp19 RF DNA (BRL) was cleaved with the same two endonucleases and the ends were subsequently dephosphorylated in 100 µl of 10 mM Tris pH 8.0 buffer with 100 units of bacterial alkaline phosphatase. A ligation was performed using 50 ng of the treated vector DNA and 12 ng of the aFGF gene fragment DNA in 10 µl of 25 mM Tris pH 7.8, 10 mM MgCl$_2$, 1 mM DTT, 0.4 mM ATP, with 2 units of T4 DNA ligase for 16 hours at 4° C. The reaction mixture was diluted 1:5 in H$_2$O and 1 µl of dilution was used to transform 20 µl of competent *E. coli* DH5 cells (BRL) as described by the supplier. The cells were plated with *E. coli* JM105 (Pharmacia) host cells in 0.03% X-gal and 0.3 mM IPTG; after incubation at 37° C. colorless plaques were isolated. One phage clone containing the bovine aFGF gene was selected, M13mp19-baFGF.

Eight oligonucleotides were designed to specify the human sequence and synthesized, see Table IX. Oligomer 8 contains an additional mutation in which thymine at site 386 in the bovine gene is replaced by cytosine in the human gene. This mutation allows the incorporation of a restriction site without altering the human aFGF amino acid sequence.

The human oligomers 1, 2, 3, 4, 6, and 8 were phosphorylated and 15 pmoles of each were annealed individually to 0.5 pmole of M13mp19-baFGF single-stranded phage DNA in 10 µl of 20 mM Tris pH 7.5, 10 mM MgCl$_2$, 50 mM NaCl, 1 mM DTT for 10 minutes at 65° C. followed by 10 minutes at 23° C. Closed-circular double-stranded molecules were then prepared in 20 µl of 20 mM Tris pH 7.5, 10 mM MgCl$_2$, 25 mM NaCl, 5.5 mM DTT, 0.5 mM ATP, 0.25 mM dATP, 0.25 mMd CTP, 0.25 mM dGTP, 0.25 mM dTTP, using 1 unit of T4 DNA ligase and 2 units of DNA polymerase I klenow fragment by incubation at 15° C. for 17 hours. The preparations were each used to transform competent JM105 cells and the resulting transformant plaques were selected by hybridization with the appropriate oligomer which had been radio-labeled using $^{32}$P-ATP and polynucleotide kinase. The conditions of hybridization were optimized for each probe to prevent formation of hybrids containing single base changes. Single-stranded DNA was isolated from the phage clone containing the human oligomer 4 mutations and the above procedure was repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations., respectively, were eluted from the gel. Approximately 60 fmoles of each fragment were collectively ligated to about 60 fmoles of a gel-purified 3.7 kb EcoRI-SalI fragment from pBR322 in 5 μl of 25 mM Tris pH 7.8, 10 mM MgCl2, 1 mM DTT, 0.4 mM ATP, with 1.5 units of T4 DNA ligase for 16 hours at 12° C. The reaction mixture was diluted 1:5 in H2O and 1 μl of dilution was used to transform 20 μl of competent E. coli DH5 cells (BRL) as described by the supplier. A clone containing the mutations specified by all four mutant oligomers was selected by hybridization with radiolabeled probes prepared from each of the oligomers. The 140 bp KpnI-BamHI DNA fragment isolated from cleaved RF DNA of the human 3 mutant M13 clone was ligated to endonuclease cleavage products of this human 1-2-6-8 mutant DNA and transformed into DH5 competent cells to generate a clone with the human 1-2-3-6-8 mutations. BamHI-PstI digestion fragments of this latter clone were ligated to the BamHI-PstI digestion fragments of RF DNA from the human 4-5 M13-based clone and the ligation mixture was used to transform DH5 competent cells. A clone containing the human 1-2-3-4-5-6-8 mutations was selected by oligomer hybridization and the aFGF gene EcoRI-SalI DNA fragment of this recombinant plasmid was ligated to phosphatase-treated EcoRI-SalI-cleaved RF DNA of M13mp18 (BRL). Competent DH5 cells were transformed with this ligated DNA and the transformed cells were plated on JM105 host cells to generate an M13 clone. The single-stranded phage DNA of this clone was annealed with the human 7 oligomer and an M13 clone containing all the desired mutations was obtained following the procedure described above. RF DNA was prepared from this clone and cleaved with EcoRI and SalI. The resulting 440 bp band was gel purified and ligated to the 2.7 kb EcoRI-SalI DNA fragment of the pKK2.7 tac promoter expression vector. This DNA was used to transform competent DH5 cells thus generating the human pKK-aFGF expression clone used for production of the human form of aFGF.

EXAMPLE 4

Mutagenesis of the Cysteine Codons of the aFGF Gene

A human aFGF single-stranded bacteriophage recombinant clone, M13mp18-haFGF, from Example 3 was mutagenized using procedures reported by Zoller and Smith, Methods in Enzymology, 100: 468–500 (1983); Norris et al., Nucleic Acids Research, 11: 5103–5112 (1983); and Zoller and Smith, DNA, 3: 479–488 (1984). Three oligonucleotides were designed to specify serine codons in place of each of the cysteine codons of the human aFGF gene at positions 16, 83, and 117. The oligomers synthesized are shown in Table XI with the mutated bases underlined.

The oligomers were phosphorylated and 15 pmoles of each were annealed individually to 330 ng of M13mp18-haFGF single-stranded DNA in 10 ul of 20 mM Tris pH 7.5, 10 mM MgCl2, 50 mM NaCl, and 1 mM DTT for 10 minutes at 65° C. followed by 10 minutes at 23° C. A second strand of DNA was synthesized using the annealed oligomer as primer in 20 ul of 20 mM Tris pH 7.5, 10 mM MgCl2, 25 mM NaCl, 5.5 mM DTT, 0.5 mM ATP, 0.25 mM dATP, 0.25 dCTP, 0.25 mM dGTP, 0.25 mM dTTP, using 3 units of T4 DNA ligase and 0.4 units of DNA polymerase I klenow fragment by incubation at 12° C. for 17 hours. The three preparations were each diluted 1:5 in H2O and 1 ul of dilution was used to transform 20 ul aliquots of competent E. coli DH5 cells (Bethesda Research Labs) as described by the supplier. The transformed cells where plated with a lawn of E. coli JM105 cells which act as host cells for the M13 virus. The resulting transformant plaques were selected by hybridization with the appropriate oligomer which had been radio-labeled using $^{32}$P-ATP and polynucleotide kinase. The conditions of hybridization were optimized for each probe to prevent retention of hybrids containing single base changes.

Single-stranded DNA was isolated from phage clones containing each of the cysteine-to-serine mutations for DNA sequence analysis using the dideoxynucleotide chain termination method of Sanger et al., Proc. Natl. Acad. Sci. USA 74: 5463–5467 (1977). RF DNAs were then prepared from three clones, each containing one of the specified mutations, and after cleavage with EcoRI and SalI the released FGF gene inserts were isolated by agarose gel electrophoresis. The purified 440bp inserts were each ligated to the 2.7 kb EcoRI-SalI DNA fragment of the pKK2.7 tac promoter expression vector in 10 ul of 25 mM Tris pH 7.8, 10 mM MgCl2, 1 mM DTT 0.4 mM ATP, with 3 units of T4 DNA ligase for 2 hours at 14° C. The ligated DNAs were used to transform competent DH5 cells and clones containing DNA with the mutated Cys codons were selected by hybridization to the appropriate oligomer. The FGF gene insert in the plasmid DNA of these clones was sequenced completely by the chemical method of Maxam and Gilbert, Methods in Enzymology 65: 499–560 (1980). One clone contained only the single base change from the original human aFGF expression clone generating a serine codon in place of a cysteine codon at position 83 and is designated as pKK-haFGF(Ser 83).

The clones containing each of the other two cysteine-to-serine mutations also contained additional non-specified changes. In order to generate the desired single base mutants the following ligations and transformations were performed. The 410 bp HindIII-derived DNA fragment of the clone with the serine codon at position 16 was isolated and ligated to the 2.7 kb HindIII-derived fragment of the original pKK-haFGF expression clone. The 230 bp NcoI-SalI-derived DNA fragment of the clone containing the serine codon at position 117 was isolated and ligated to the 2.9 kb NcoI- SalI-derived fragment of pKK-haFGF. Each of these ligated samples was used to transform competent DH5 cells; hybridization and sequencing techniques were used to identify the other two desired single base mutants designated pKK-haFGF(Ser 16) and pKK-haFGF(Ser 117). These three clones were used for production of the Ser 16, Ser 83, and Ser 117 forms of the human aFGF.

Site-directed mutants of human aFGF with two or three cysteine (Cys) residues converted to serine (Set) residues were constructed by combining restriction fragments of the non-mutated wild-type and the Ser (16), Ser (83) and Ser (117) mutant synthetic genes, have been cloned in pKK2.7 and subcloned in M13mp18, as described above. The pKK-haFGF (Ser 16,83) and pKK-haFGF (Ser 16,117) recombinants were constructed first by introducing the 0.23 Kb EcoR1-BamH1 fragment of M13mp18 (Ser 16), that includes the codon for Ser 16, into pKK2.7 followed by insertion of the 0.2 Kb BamH1-SalI fragments either from M13mp18 (Ser 83) or from M13mp18 (Ser 117). Since the pKK2.7 vector contains two BamH1 sites, one in the multicloning sequence and the second one upstream of the tac promoter, a modified pKK2.7 vector, in which the second upstream BamH1 site was eliminated, was used in these constructions. After digestion with the corresponding restriction enzymes, subsequent ligation and transformation of AB1899 competent cells (*E. coli* Genetic Stock Center), ampicillin resistant clones were selected and screened for those containing plasmids with the expected molecular weight for the recombinants (3.1 Kb).

The mutant haFGF (Ser 16,83,117) was constructed by replacing the 0.13 Kb Sphl-SalI fragment of pKK-haFGF (Ser 16,83), by the corresponding fragment of pKK (Ser 117) that encodes for Ser instead of Cys in position 117. The 3 Kb Sphl-SalI fragment of pKK (Ser 16,18) was purified by preparative agarose gel electrophoresis, electroelution and ligated to the 0.13 Kb Sphl-SalI fragment of pKK (Set 117) purified from a 5% polyacrylamide gel in the same way. The purified fragments were ligated and recombinats were selected for ampicillin resistance after transformation of AB1899 cells.

For construction of pKK-haFGF (Ser 83,117), the 0.3 Kb Pstl fragment of pKK haFGF was replaced with the same fragment of pKK-haFGF (Ser 16,83,117) that includes the codons for Ser instead of Cys at positions 83 and 117 using basically the same strategy. AB1899 transformants selected for ampicillin resistance were analyzed by Pstl-SalI digestion to determine the orientation of the ligated fragments. All mutant genes were sequenced by the dideoxy method using the Sequence kit of USB Corp.

EXAMPLE 5

Expression of the Synthetic Bovine aFGF Gene

The intact aFGF genes from Example 4 were incorporated into a modified pKK223-3 plasmid. The pKK223-3 plasmid (Pharmacia) contains the tac promoter which is a hybrid between regions of the trp promoter and the lac promoter, deBoer et al., Proc. Natl Acad. Sci. USA 80: 21–25 (1983). This plasmid also contains the rrnB rRNA transcription terminator, a strong terminator sequence found to allow expression from strong promoters, Gentz et al., Proc. Natl. Acad. Sci. USA 78: 4936–4940 (1981); Brosius, Gene 27: 161–172 (1984). The pKK223-3 plasmid was modified to remove the pBR322-derived SalI restriction enzyme site. This was accomplished by cleaving the pKK223-3 plasmid DNA with NdeI and NarI, blunt-ending the DNA fragment with Klenow DNA polymerase, and recircularizing the 2.7 kb DNA fragment to generate clone pKK2.7. The synthetic aFGF gene was then cleaved from its pBR322 vector and transferred to pKK2.7 after restricting this expression vector with EcoRI and SalI. This construction positions the initiating methionine of the synthetic gene 11 bases downstream of the Shine-Dalgarno ribosome binding site. The resulting recombinant vectors, as exemplified by FIG. 1, were transformed into *E. coli* JM105 cells and also into *E. coli* DH5 cells.

The expression clones were grown at 37° C. in LB broth (1% tryprone, 0.5% yeast extract, 0.5% NaCl) containing 0.4% glucose and 50 μg/ml ampicillin. When the optical density at 550 nm reached 0.5, IPTG was added to give 1 mM and growth was continued at 37° C. for 3 hours. The cells were harvested by centrifugation at 10,000×g for 20 minutes and the cells from 1 liter of culture were resuspended in glycerol/phosphate buffered saline 1:1 and quickly frozen in a dry ice/ethanol bath and stored overnight at −70° C.

EXAMPLE 6

Enhanced Expression Vector

Enhanced levels of expression for the mutated forms of aFGF of Example 4 were provided by modification of the expression vector of Example 3 to introduce an additional cistron upstream of the aFGF encoding sequence. Two oligonucleotides were synthesized with the sequences as shown at page 40. When annealed these oligomers supply 5' extensions of 4 bases which are complementary to the extensions provided by EcoR1 cleavage, a 7 codon open reading frame following the ATG translation initiation codon and preceding a TAA stop codon, and an additional Shine-Dalgarno ribosome binding site located within the open reading frame upstream of the stop codon. Using 1 pmole of each oligomer, the oligomers were annealed together in 20 μl of DNA ligase buffer by heating to 70° C. for 10 minutes and slow cooling. The annealed mixture, 0.3 pmole, was ligated to 0.1 pmole of EcoR1-cleaved pKK-haFGF plasmid DNA in a final volume of 25 μl containing 3 units of T4 DNA ligase (Pharmacia) for 2.5 hours at 14° C. The ligated DNA, 5 ng, was used to transform competent *E. coli* JM105 cells. The transformants were screened by restriction analysis, as the EcoR1 site is lost by this insertion, and by immunoblot analysis. The expression vector of one clone, which demonstrated higher levels of FGF production, was sequenced by the chemical technique of Maxam and Gilbert, supra, to verify the correct insertion of the new cistron sequences. Subsequently, this high expression pKK2c-haFGF vector was transfered to *E. coli* DH5 by transformation procedures.

In order to express the haFGF (Ser 117) mutant gene, for example, in this high expression vector, the 0.23 kb NcoI-SalI fragment of pKK-haFGF (Ser 117) was ligated to the 2.5 kb NcoI-SalI fragment of pKK2c-haFGF and transformed into competent cells. The other mutated haFGFs were transferred to the two cistron high expression vector in a similar manner, replacing appropriate restriction fragments containing the wild-type sequences of pKK2c-haFGF with the analogous restriction fragments of the mutated haFGF.

EXAMPLE 7

Extraction and Purification-of Mutated aFGF

The frozen cells from Example 5 were thawed and resuspended in a quantity sufficient to make 50 ml with 100 mM phosphate buffer, pH 7.2, 5 mg/ml EDTA and the cells were collected by centrifugation at 28,000×g for 5 minutes. The cells were washed a second time, collected by centrifugation and resuspended in 50 ml of the same buffer. The extinctions of the three mutant strain suspensions at 660 nm were strain pKK-haFGF(Ser 117), 103; strain pKK-haFGF(Ser 16), 108; strain pKK-haFGF(Ser 83) 59. Each sample received 0.1 mg/ml of lysozyme and was incubated for 15 minutes with gentle shaking at 30° C. The cells were collected by centrifugation and resuspended in 50 ml of breaking buffer consisting of 100 mM phosphate; pH 6.0; 3 mM, EDTA; 0.05 mM, TPCK, 0.05 mM, Pepstatin A, 0.05 mM, Leupeptin and 15 μg/ml BPTI. Each cell suspension was kept at 4° C. and broken by two passages through a previously cooled French pressure cell at 20,000 psi at 4° C. The disrupted cell suspensions were centrifuged for 15 minutes at 15,000 rpm in a SS-34 Sorvall rotor and for 60 minutes at 45,000 rpm in a 70 Ti rotor in a Beckman ultracentrifuge at 4° C. The supernatant fluid was collected, the extinctions at 280 nm for a 55 ml volume were determined: pKK-haFGF(Ser 117), 44; pKK-haFGF(Ser 16), 40 and pKK-haFGF(Ser 83), 23 and the samples were frozen at −70° C.

The supernatant fluids were thawed by the addition of 200 ml of 100 mM phosphate buffer, pH 6.0, containing CM-Sephadex at a ratio of 6.5 ml of settled resin per gram of protein (assuming absorbance through a 1 cm path of a 1 mg/ml protein solution is 1.0). The sample was collected in a scintered glass funnel and washed three times with 200 ml of 100 mM phosphate buffer containing 150 mM NaCl at a pH of 6.0. The resin cake was resuspended in 200 ml of the same buffer, packed in a column at 12 ml×hr$^{-1}$ per cm$^2$ crossectional ArGA and washed at the same flow rate with 150 mM phosphate buffer containing 600 mM NaCl. The fractions containing the protein eluted with the 600 mM NaCl buffer were pooled, the pH adjusted to 7.2 and the conductivity adjusted with deionized water to 10 μS×cm$^{-1}$. Heparin-Sepharose (freshly prepared) equilibrated with 10 mM phosphate pH 7.2 (conductivity 1.3 μS×cm$^{-1}$) was then added at a ratio of 1 ml of settled resin per mg of protein (using the same assumed extinction coefficient as above), the suspension gently shaken for one hour at 4° C., and the resin collected in a funnel, resuspended in the same buffer and packed in a column at 1-2 column volume per hour. The packed column was washed with 10 mM phosphate, 0.8 M NaCl pH 7.2 at the same flow rate until the extinction of the eluate at 280 nm decreased to a steady value, to within 0.01 optical absorbance units above the elution buffer and then the buffer changed to 10 mM phosphate, 1.5 M NaCl pH 7.2. The fractions containing the protein eluted with the 1.5 M buffer (monitored by the extinction at 280 nm) were pooled together and loaded in a C$_3$ reversed phase HPLC column equilibrated with 10 mM TFA and eluted with a gradient from 0–67% CH$_3$CN in 30 minutes.

The purification data of the mutant strains is shown below:

pKK-haFGF(Ser 16)

Fractions 25-31 eluted from the CM-Sephadex column with the 0.6 M NaCl buffer in a total volume of 24 ml and a protein content of 3.5 mg were made 125 ml with deionized water (final conductivity: 7 mS/cm) and 4 ml of heparin-Sepharose added. The column was run at 6 ml/h. Fractions 55-57 eluted with 1.5 M NaCl, were injected on the C$_3$ column. From this column a major peak was collected with a protein content of 80 μg.

pKK-haFGF(Ser 83)

Fractions 19-33 eluted from the CM-Sephadex column with the 0.6 M NaCl buffer in a total volume of 40 ml and a protein content of 4.0 mg were made 150 ml with deionized water (final conductivity: 10 mS/cm) and 4 ml of heparin-Sepharose added. The column was run at 6 ml/h. Fractions 40-44, eluted with 1.5 M NaCl, were injected in the C$_3$ column. From this column a major peak was collected with a protein content of 80 μg.

pKK-haFGF(Ser 117)

Fractions 19-33 eluted from the CM-Sephadex column with the 0.6 M NaCl buffer in a total volume of 57 ml and a protein content of 11.4 mg were made 250 ml with deionized water (final conductivity: 12 mS/cm) and 10 ml of heparin-Sepharose added. The column was run at 11 ml/h. Fractions 59-62, eluted with 1.5 M NaCl, were injected in the C$_3$ column. From this column a major peak was collected with a protein content of 614 μg.

The protein products of the multiple mutants were purified by the same procedures. All forms of aFGF, recombinant wild-type and the mutants were highly purified since only single 16 kDa bands were seen following reduction and electrophoresis in SDS 15% polyacrylamide gels at loads 100-fold above the threshold of detection.

EXAMPLE 7

Biological Activity of Mutated aFGF

Biological activity of the purified r-aFGF from Example 6 was evaluated using a fibroblast mitogenic assay modified from Thomas et al., J. Biol. Chem. 225: 5517-5520 (1980). BALB/c 3T3 A31 fibroblasts (American Type Culture Collection) were plated at 3×10$^4$ cells per 100 μl per well in 96-well culture dishes in culture media containing 10% heat-inactivated calf serum and incubated in 7% CO$_2$ (pH 7.35±0.05). The cells became fully quiescent by replacing the media with 1.0% heat-inactivated calf serum 6 and again 24 hours later. At 55 hours after plating, 10 μl of test sample with or without 5 μg of heparin and 0.11 μg of dexamethasone were added, at 70 hours each well was supplemented with 0.2 μCi of [methyl-$^3$H]-thymidine (20 Ci/mmole, New England Nuclear) and 0.3 μg of unlabeled thymidine (Sigma), and at 95 hours the cells were processed for determination of radiolabel incorporated into DNA. Each dose-response point was the average of four determinations. The results of Ser-117 Mutant, the only mutant form showing activity equal to or greater than wild type, are shown in the following table:

TABLE XII

Mitogenic Responses of BALB/c 3T3 Fibroblasts to Mutated aFGF

| Dose (amt/ml) | Wild type −heparin | Wild type +heparin | Ser-117 Mutant −heparin | Ser-117 Mutant +heparin |
|---|---|---|---|---|
| 3.16 pg | 1449 | 724 | 2055 | 883 |
| 10.0 pg | 1917 | 914 | 2662 | 1255 |
| 31.6 pg | 1547 | 1007 | 3076 | 2748 |
| 100 pg | 2263 | 2498 | 4833 | 8067 |
| 316 pg | 2647 | 14945 | 11505 | 44193 |
| 1.00 ng | 3975 | 54516 | 22869 | 66778 |
| 3.16 ng | 6400 | 68447 | 40487 | 60306 |
| 10.0 ng | 12665 | 61294 | 54163 | 56326 |
| 31.6 ng | 21843 | 56552 | 70670 | 59854 |
| 100 ng | 44744 | 66816 | 66802 | 63856 |

The 4 titration curves are compared at their half-maximal rise. The WT in the absence of heparin does not reach a peak so the same peak magnitude is assumed as seen for the other 3 peaks and the half-maximal value extrapolated.

TABLE XIII

Comparison of Concentrations Necessary for Half Maximal Stimulation

| Sample | Heparin | Conc. of ½ maximal stimulation |
|---|---|---|
| WT | − | 66 ng/ml |
|  | + | 0.56 ng/ml |
| Ser-117 Mutant | − | 2.3 ng/ml |
|  | + | 0.20 ng/ml |

All dilutions were prepared from a stock solution containing 1.51 mg/ml of purified reactants. The Ser-117 mutant is at least as active as the wild type in the presence of heparin. The activity of the wild type is about 10-fold more dependent on heparin than the mutant consequently 90% of the heparin dependence of WT aFGF is eliminated in the Ser-117 mutant.

The mitogenic assay used to evaluate biological activity was modified so that mutated and wild-type aFGF could be compared. Heat-inactivated calf serum was replaced with 1% insulin-selenium-transferin (ITS), 0.4 gm L-histidine, 50 µl of 1 M ethanolamine, 1.25 gm bovine serum albumin with 5.35 mg of linoleic acid per liter of 75% DMED, 25% Ham's F12 containing both penicillin-streptomycin and L-glutamine as described above. Full dose-response assays were done as described above at consecutive two-fold dilutions over at least 3 log orders of aFGF concentration spanning the complete rise of the response from background through peak DNA synthesis levels. All concentration points were done in quadruplicate on confluent Balb/c 3T3 cells in 96 well dishes. One stimulatory unit was calculated as the amount of aFGF per ml that generated a half-maximal response. The specific mitogenic activity is the number of such stimulatory untis per mg of pure aFGF. All samples of aFGF were prediluted to 50 µg/ml in the same TFA/CH$_3$CN solvent. The activities of wild-type and mutated aFGF are compared in the following table.

TABLE XIV

| Sample | With Heparin | Without Heparin | Fold Increase |
|---|---|---|---|
| WT | 5.37 ng/ml (0.186 × 10$^6$) | 269 pg/ml (3.72 × 10$^6$) | 20.0 |
| Ser 16 | 33.9 ng/ml (0.030 × 10$^6$) | 400 pg/ml (2.50 × 10$^6$) | 84.8 |
| Ser 83 | 4.36 ng/ml (0.229 × 10$^6$) | 251 pg/ml (3.98 × 10$^6$) | 17.4 |
| Ser 117 | 182 ng/ml (0.549 × 10$^6$) | 240 pg/ml (4.17 × 10$^6$) | 7.58 |
| Ser 16,83 | 800 pg/ml (1.25 × 10$^6$) | 195 pg/ml (5.13 × 10$^6$) | 4.10 |
| Ser 16,117 | 741 pg/ml (1.35 × 10$^6$) | 148 pg/ml (6.76 × 10$^6$) | 5.01 |
| Ser 83,117 | 295 pg/ml (3.39 × 10$^6$) | 100 pg/ml (10.0 × 10$^6$) | 2.95 |
| Ser 16,83,117 | 427 pg/ml (2.34 × 10$^6$) | 107 pg/ml (9.35 × 10$^6$) | 3.99 |

Figure 2A:
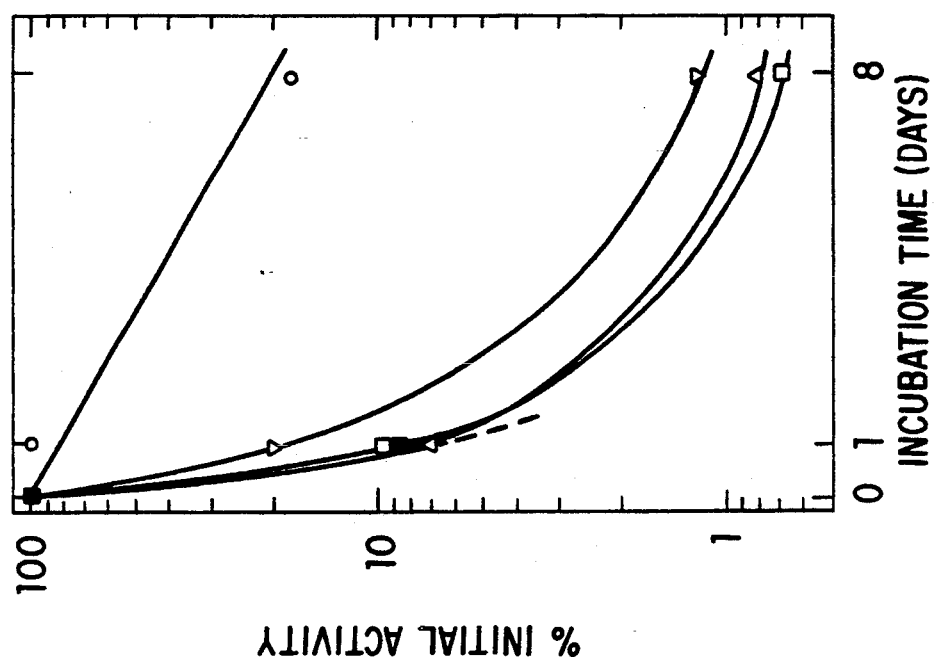
FIG. 2(A) and (B) demonstrate the stability of recombinant wild type haFGF and mutant haFGF measuring mitogenic activity versus time in the presence of heparin (A) and absence of heparin (B).
Figure 2B:
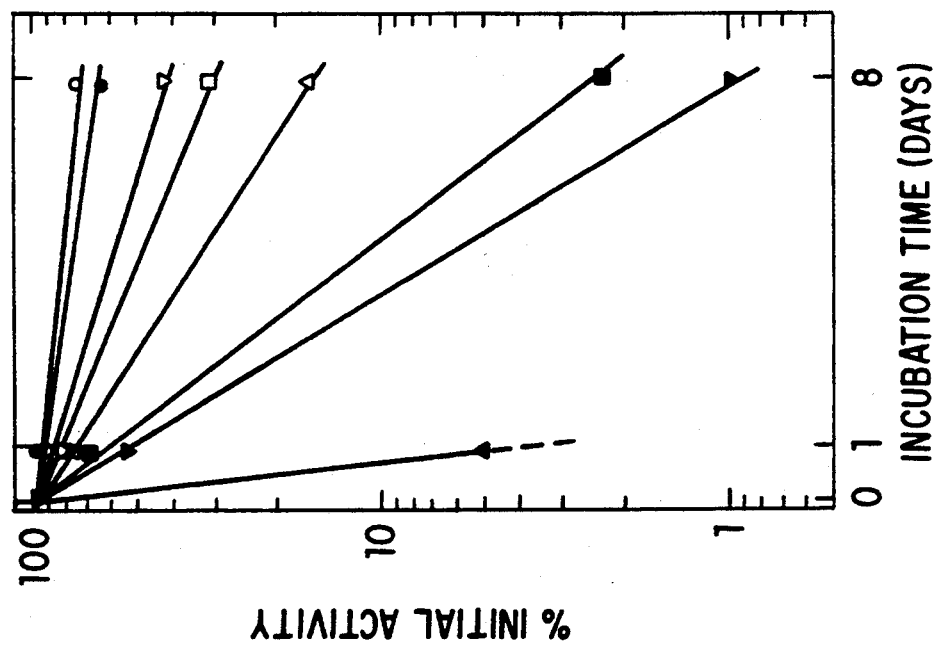

The relative stabilities of the recombinant wild-type haFGF, the single Ser mutants and the multiple Ser mutants were determined. Mitogenic activites were measured following 0, 1 and 8 day incubations in serum-free DME solutions, normally used for serial sample dilutions, that were C$_2$O-buffered to pH 7.3 at 37° C. containing 1 mg/ml human serum albumin. Mitogen samples were stored at 512 ng/ml, with or without 500 µg heparin/ml, equivalent to the 10-fold concentrates from which the highest concentration point in the assay is diluted. Each sample was stored and assayed either in the presence or absence of heparin. The relative stabilities, following scaling to set each day 0 activity to 100%, are shown in FIG. 2 as a function of storage time. In FIG. 2: ▼ corresponds to wild-type; ▲ corresponds to haFGF (Ser 16); ■ corresponds to haFGF (Ser (83); ● corresponds to haFGF (Ser (117); V corresponds to haFGF (Ser 16,83); a corresponds to haFGF (Ser 16,117); □ corresponds to haFGF (Ser 83,117); and o corresponds to haFGF (Ser 16,83,117).

The loss of activity of wild-type haFGF and the mutants in the presence of heparin closely fits an exponential decay, see FIG. 4A. The activities of all the mutants except Ser (16) are more stable than the wild-type mitogen. The most stable mutants, in descending order of stability are Set 16,83,117), Set (117) Ser (16,83), Ser (83,117), Ser (16,83) and Ser (83), Ser (16). The stability of Ser (83) was only slightly higher than the wild-type. The various forms of aFGF were less stable in the absence of heparin and with the apparent exception of Ser (16,83,117), the decay appeared not to be a simple exponential of the time period.

A sample of the expression vector pKK-haFGF(Ser 117) designated A48-1a1 containing the gene capable of expressing the serine 117 mutant in E. coli DH5 was deposited in the American Type Culture Collection, 12301 Parklawn Drive, Rockville, Md. 20852 USA, on Sep. 30, 1987 under the Budapest Treaty and has been assigned ATCC number 67522.

What is claimed is:

1. A method of promoting mitogenesis which comprises administration of an effective amount of a recombinant human mutant microheterogeneous form of acidic fibroblast growth factor wherein all three cysteine residues at positions 16, 83, and 117, numbered in accordance with a native human 140 amino acid microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

2. The method of claim 1 wherein the mutant acidic fibroblast growth factor is a 154, 140, or 139 amino acid microheterogeneous form.

3. The method of claim 1 wherein said amino acid incapable of forming intramolecular or intermolecular disulfide bonds is serine.

4. The method of claim 1 wherein the methionine residue at position 67, numbered in accordance with the native human 140 amino acid microheterogeneous form, is replaced by a non-air-oxidizable amino acid.

5. The method of claim 4 wherein the non-air-oxidizable amino acid is either alanine, valine, leucine or isoleucine.

6. The method of claim 4 wherein the non-air-oxidizable amino acid is leucine.

7. A method of promoting mitogenesis which comprises administration of an effective amount of a recombinant human mutant microheterogeneous form of acidic fibroblast growth factor wherein all three cysteine residues at positions 16, 83, and 117, numbered in accordance with a native human amino acid microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

8. The method of claim 7 wherein the mutant acidic fibroblast growth factor is a154, 140 or 139 amino acid microheterogeneous form.

9. The method of claim 7 wherein said amino acid incapable of forming intramolecular or intermolecular disulfide bonds is serine.

10. The method of claim 7 wherein the methionine residue at position 67, numbered in accordance with the native human 140 amino acid microheterogeneous form, is replaced by a non-air-oxidizable amino acid.

11. The method of claim 10 wherein the non-air-oxidizable amino acid is either alanine, valine, leucine or isoleucine.

12. The method of claim 10 wherein the non-air-oxidizable amino acid is leucine.

13. A method of promoting mitogenesis which comprises administration of an effective amount of a recombinant human mutant microheterogeneous form of acidic fibroblast growth factor wherein a cysteine at position 117, numbered in accordance with a native human 140 amino acid microheterogeneous form, is replaced with an amino acid incapable of forming intramolecular or intermolecular disulfide bonds, and optionally having an additional methionine attached to the N-terminus and wherein said mutant acidic fibroblast growth factor has greater biological activity in the absence of heparin than the native human acidic fibroblast growth factor.

14. The method of claim 11 wherein the mutant acidic fibroblast growth factor is a 154, 140 or 139 amino acid microheterogeneous form.

15. The method of claim 11 wherein said amino acid incapable of forming intramolecular or intermolecular disulfide bonds is serine.

16. The method of claim 11 wherein the methionine residue at position 67, numbered in accordance with the native human 140 amino acid microheterogeneous form, is replaced by a non-air-oxidizable amino acid.

17. The method of claim 16 wherein the non-air-oxidizable amino acid is either alanine, valine, leucine or isoleucine.

18. The method of claim 16 wherein the non-air-oxidizable amino acid is leucine.

* * * * *